United States Patent
Woodworth et al.

(10) Patent No.: US 10,278,745 B2
(45) Date of Patent: May 7, 2019

(54) INTERLAMINAR, INTERSPINOUS STABILIZATION DEVICES FOR THE CERVICAL SPINE

(71) Applicants: University of Maryland, Baltimore, Baltimore, MD (US); Paradigm Spine, LLC, New York, NY (US)

(72) Inventors: Graeme Woodworth, Baltimore, MD (US); Stephen Eckhof, Rietheim-Weilheim (DE); Sven Oliver Muckenfuß, Spaichingen (DE)

( * ) Notice: Subject to any disclaimer, the term of this patent is extended or adjusted under 35 U.S.C. 154(b) by 0 days.

(21) Appl. No.: 14/940,074

(22) Filed: Nov. 12, 2015

(65) Prior Publication Data
US 2016/0135851 A1 May 19, 2016

Related U.S. Application Data

(60) Provisional application No. 62/079,427, filed on Nov. 13, 2014.

(51) Int. Cl.
*A61B 17/70* (2006.01)

(52) U.S. Cl.
CPC ...... *A61B 17/7071* (2013.01); *A61B 17/7067* (2013.01)

(58) Field of Classification Search
CPC ............ A61B 17/7044; A61B 17/7047; A61B 17/7062; A61B 17/7065; A61B 17/7067; A61B 17/7068; A61B 17/707; A61B 17/7071; A61F 2/4405
See application file for complete search history.

(56) References Cited

U.S. PATENT DOCUMENTS

| | | | | |
|---|---|---|---|---|
| 7,837,711 B2* | 11/2010 | Bruneau | ............ | A61B 17/7055 606/246 |
| 7,922,750 B2* | 4/2011 | Trautwein | .......... | A61B 17/1606 606/279 |
| 8,252,026 B2* | 8/2012 | Joshi | .................. | A61B 17/7064 606/246 |
| 9,381,047 B2* | 7/2016 | Sheffer | ............. | A61B 17/7062 |
| 2006/0241601 A1* | 10/2006 | Trautwein | .......... | A61B 17/7049 606/248 |
| 2007/0161993 A1* | 7/2007 | Lowery | ............. | A61B 17/7055 606/279 |
| 2009/0270919 A1* | 10/2009 | Dos Reis, Jr. | ...... | A61B 17/7062 606/249 |
| 2012/0226312 A1* | 9/2012 | Thalgott | ............ | A61B 17/7062 606/246 |
| 2015/0012040 A1* | 1/2015 | Agarwal | ............ | A61B 17/7068 606/248 |

FOREIGN PATENT DOCUMENTS

WO    WO 2010122472 A1 * 10/2010    ......... A61B 17/7064

* cited by examiner

*Primary Examiner* — Julianna N Harvey
(74) *Attorney, Agent, or Firm* — Farber LLC; Tram Anh Nguyen

(57) ABSTRACT

Dynamic, rigid, and convertible dynamic-to-rigid devices and methods of using such devices to treat spinal instability conditions of the cervical spine are provided. The devices may include an interspinous, interlaminar stabilization device configured for interlaminar placement between the spinous processes of adjacent cervical vertebrae and optionally secured to the lamina using bone screws or crimped or rigidly fixed to the spinous process. Multiple devices may be used to enable treatment of multiple levels at the same time.

14 Claims, 20 Drawing Sheets

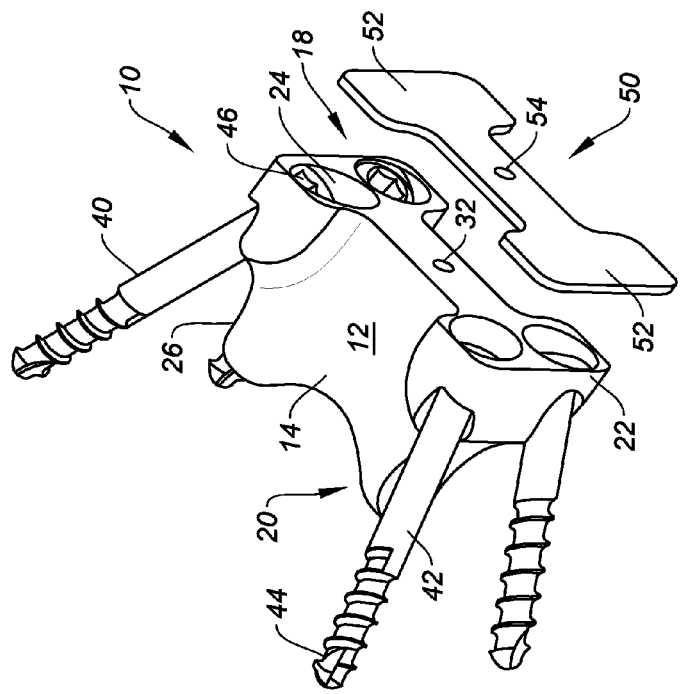
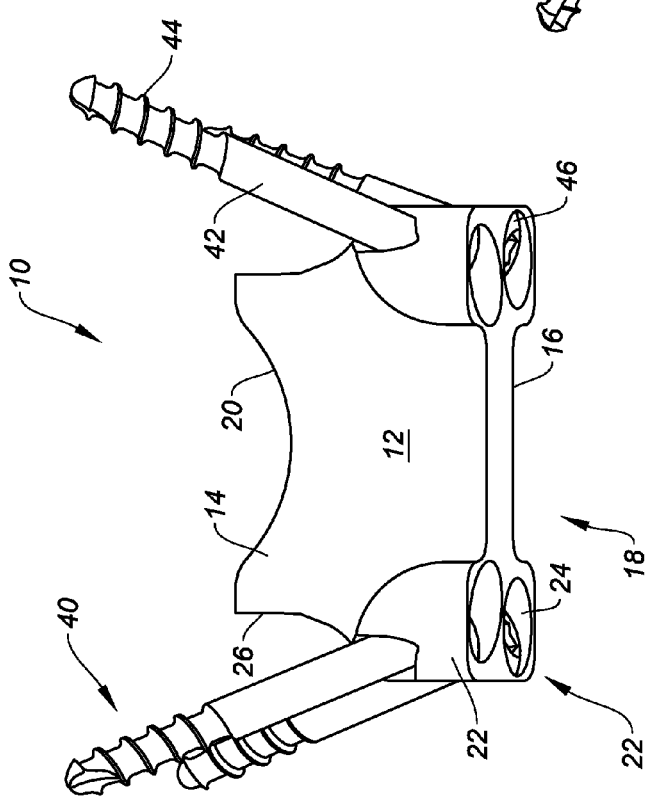
FIG. 1B
FIG. 1A

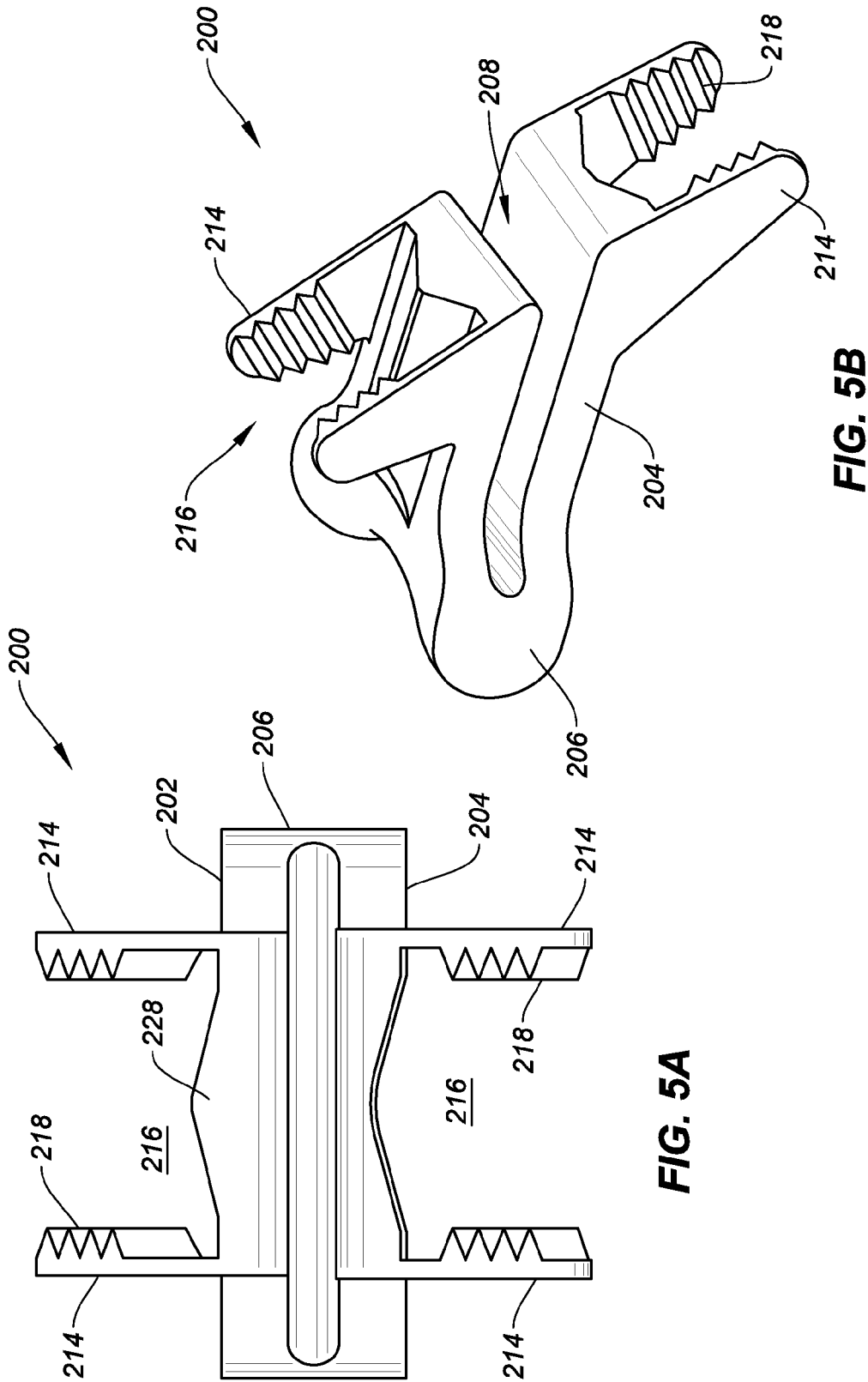

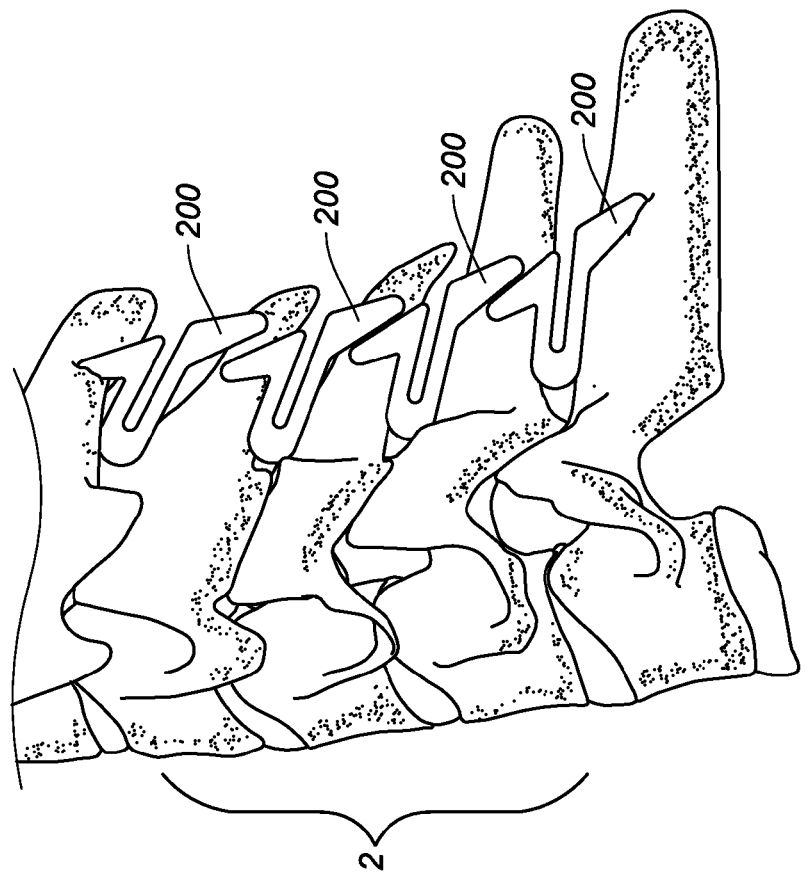
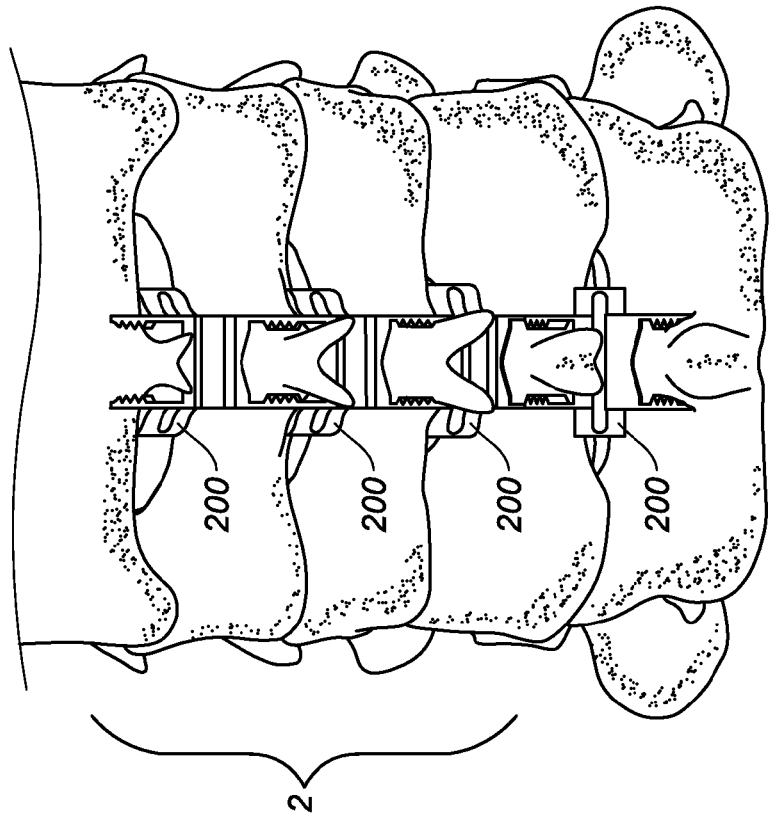
FIG. 7B
FIG. 7A

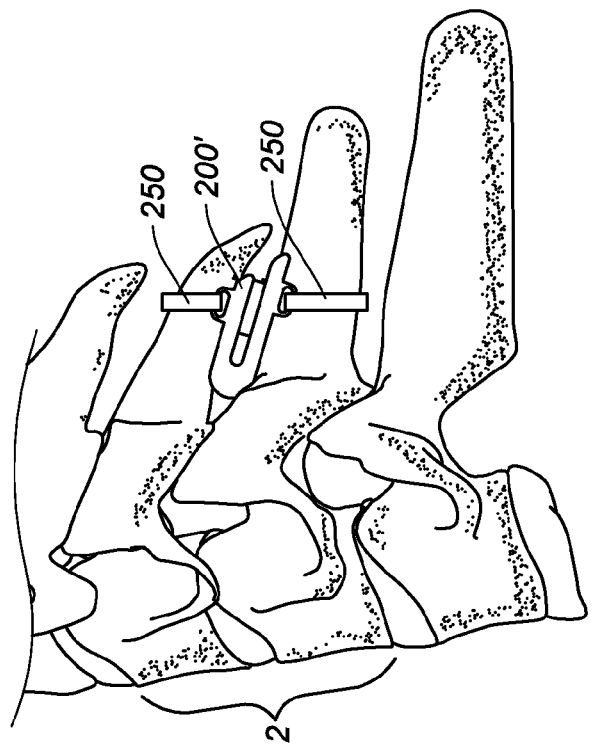
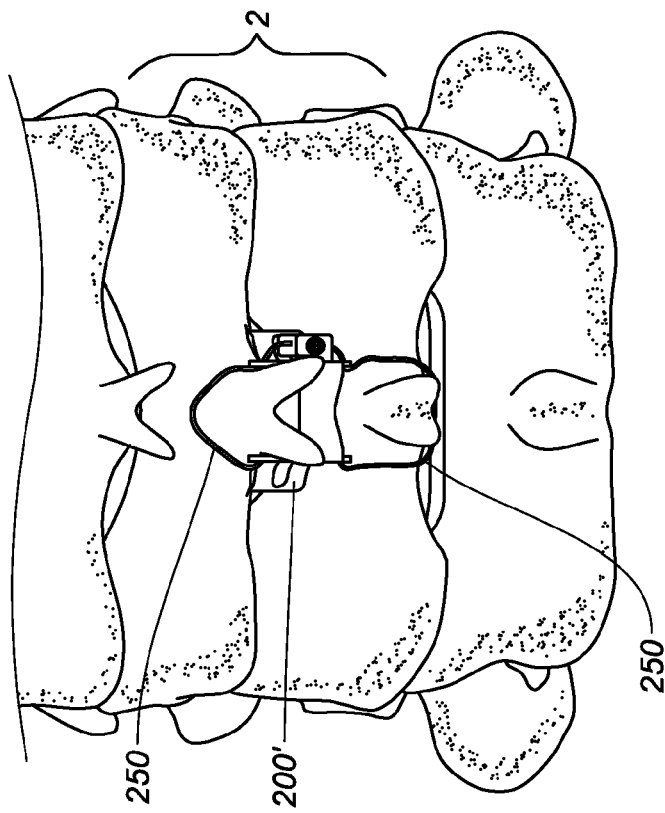
FIG. 9B
FIG. 9A

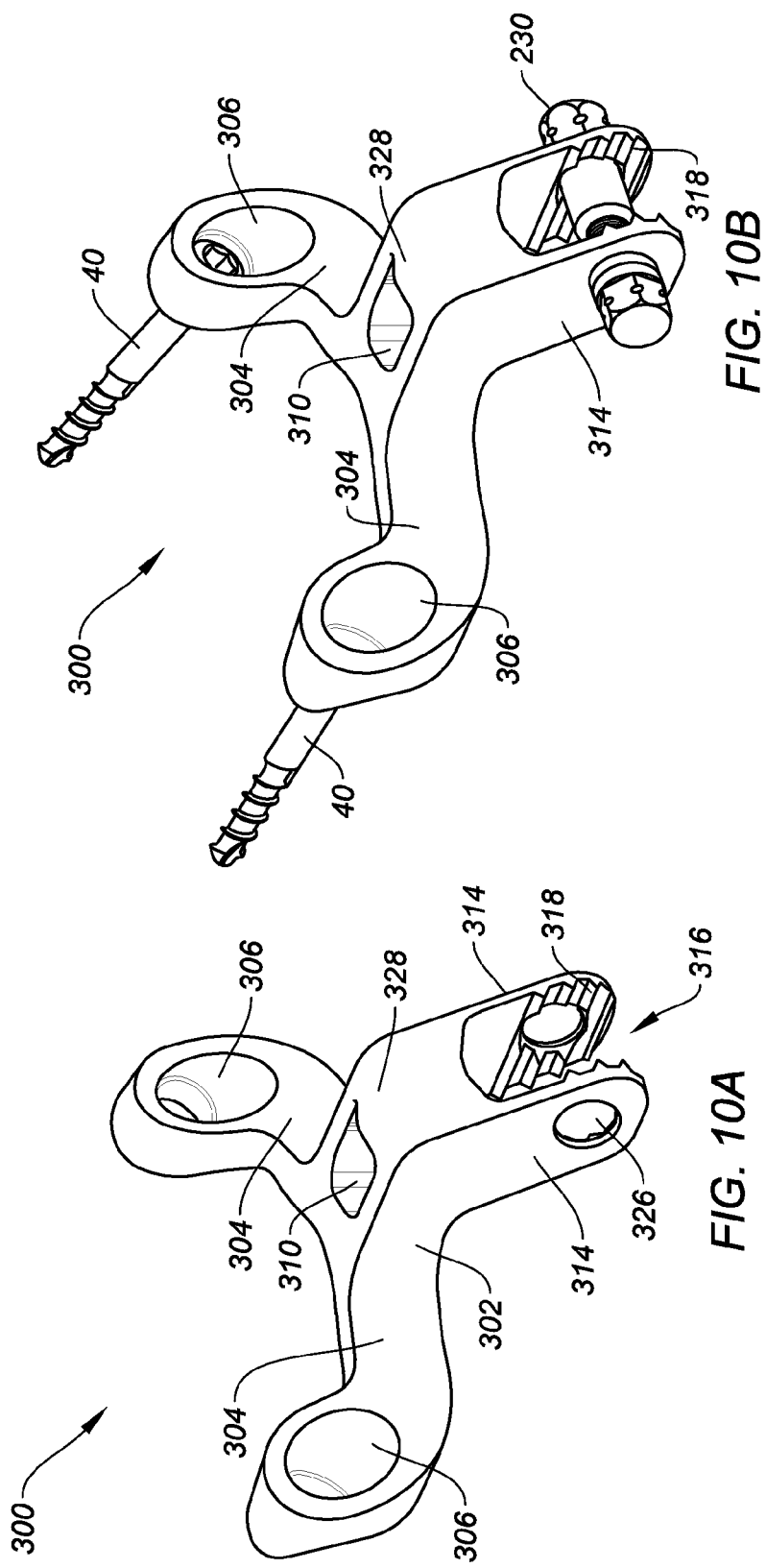

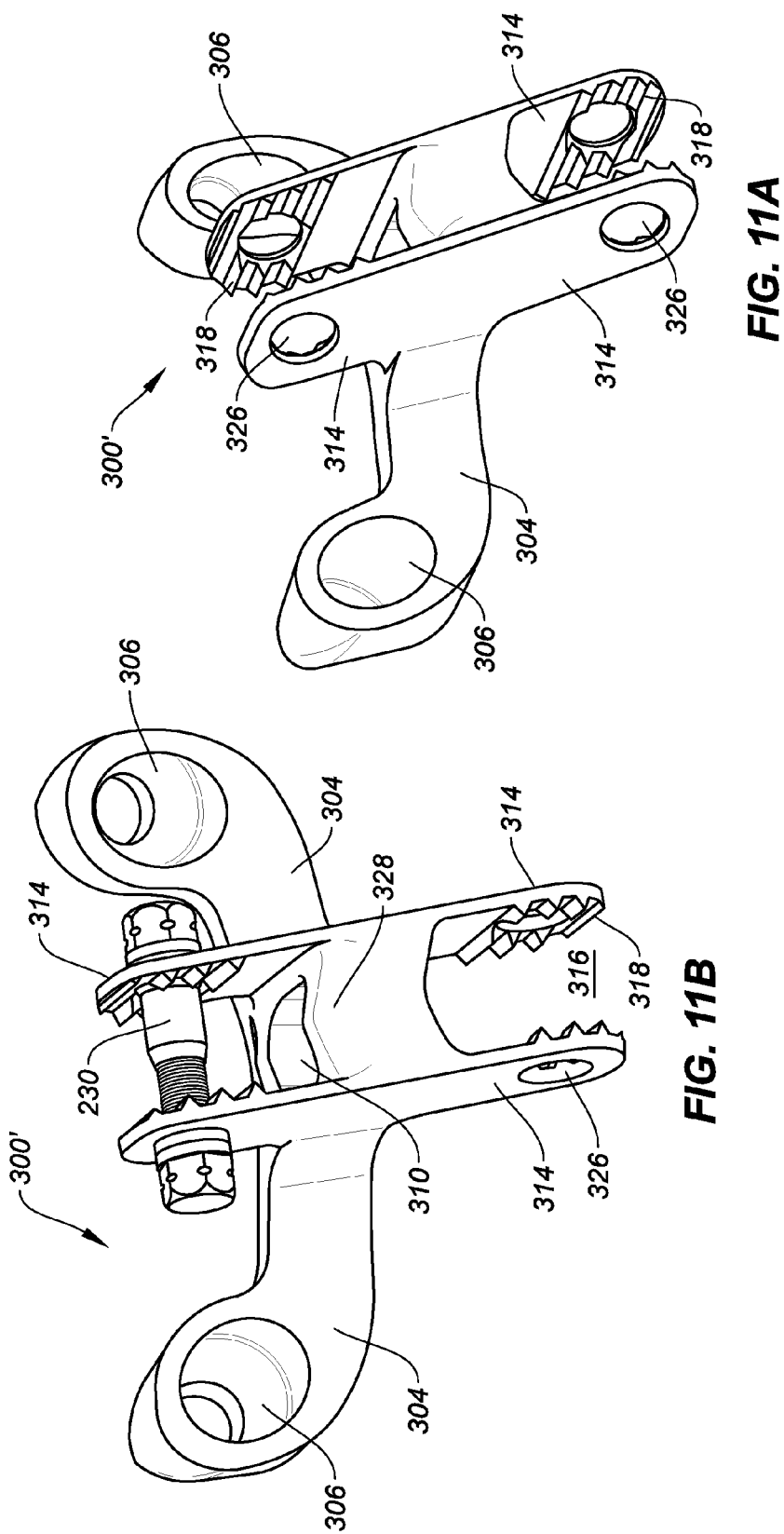

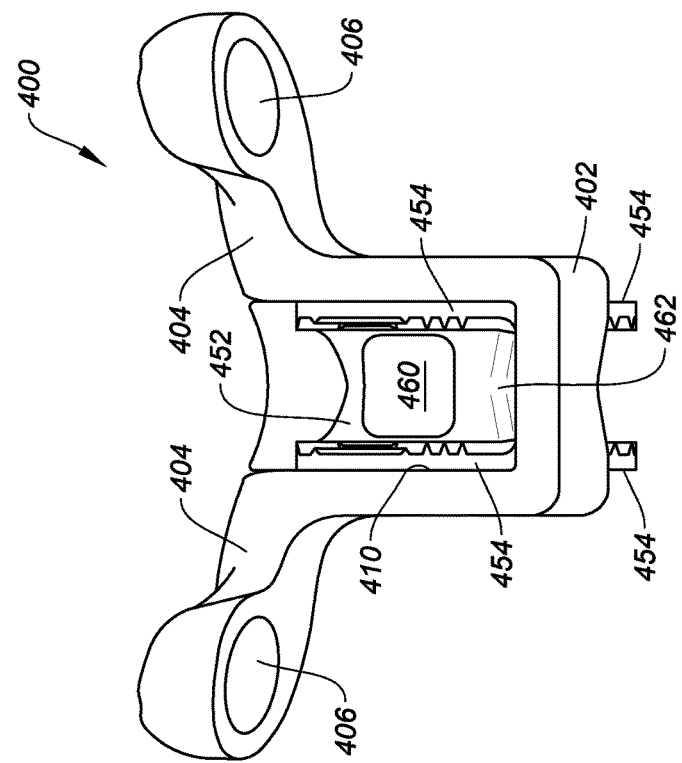
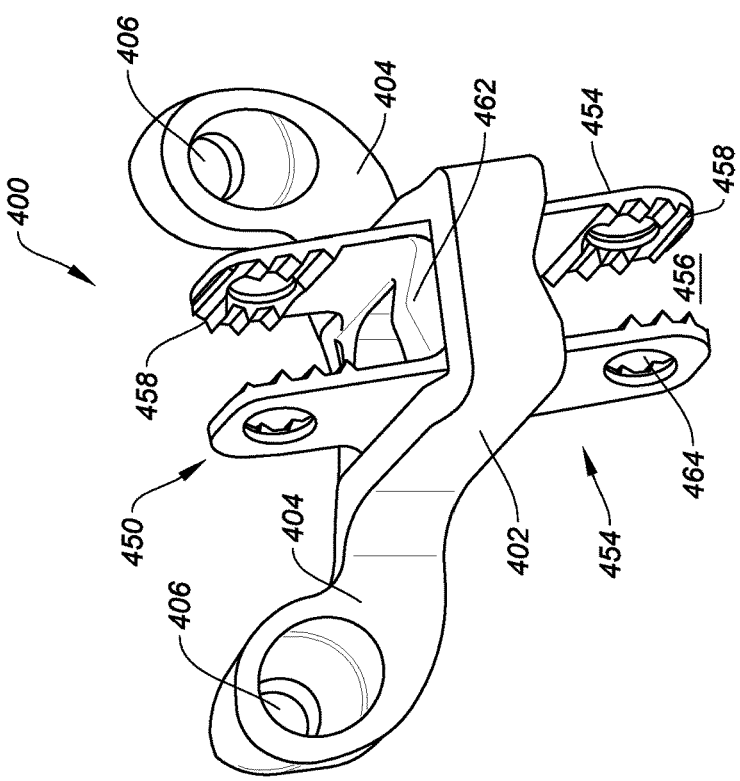

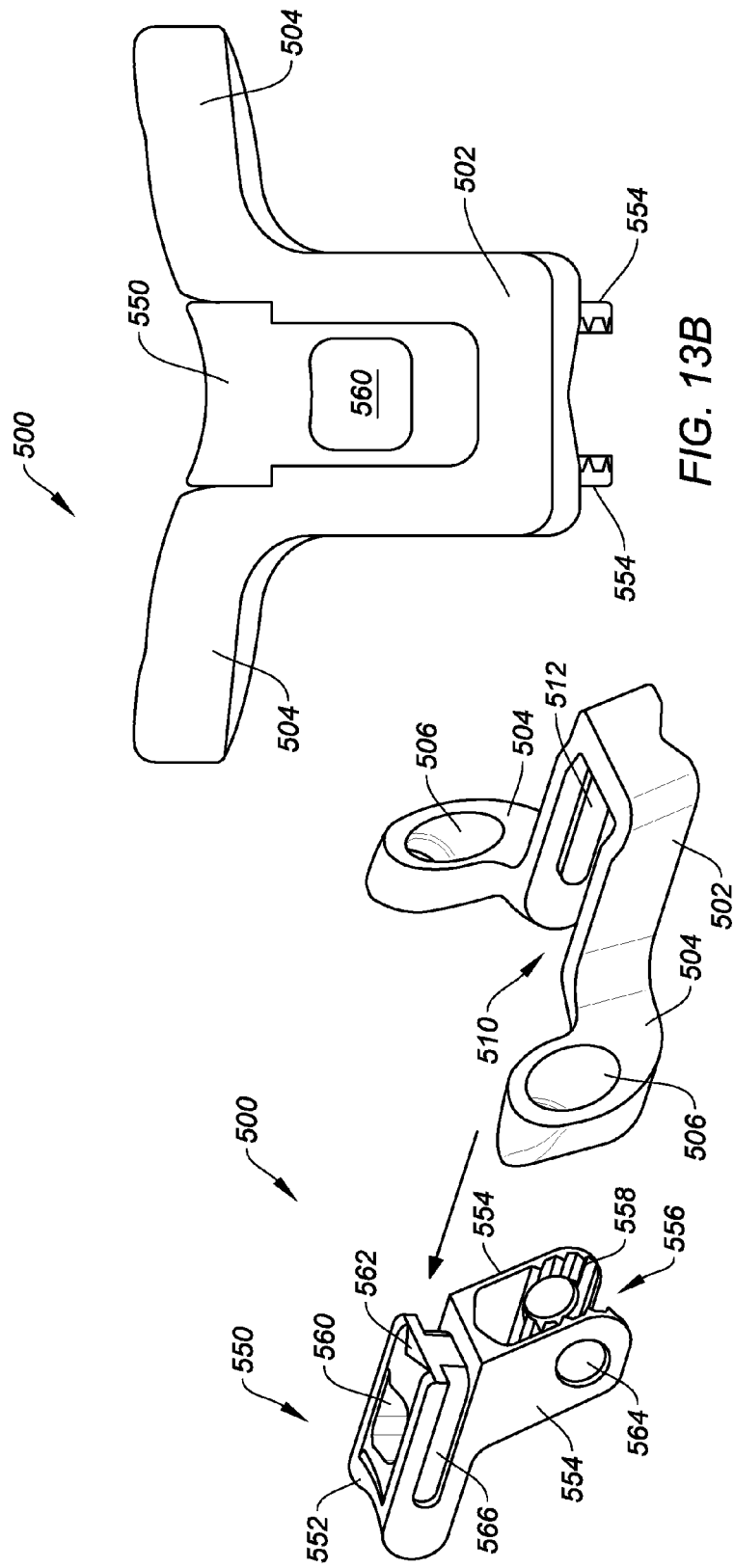

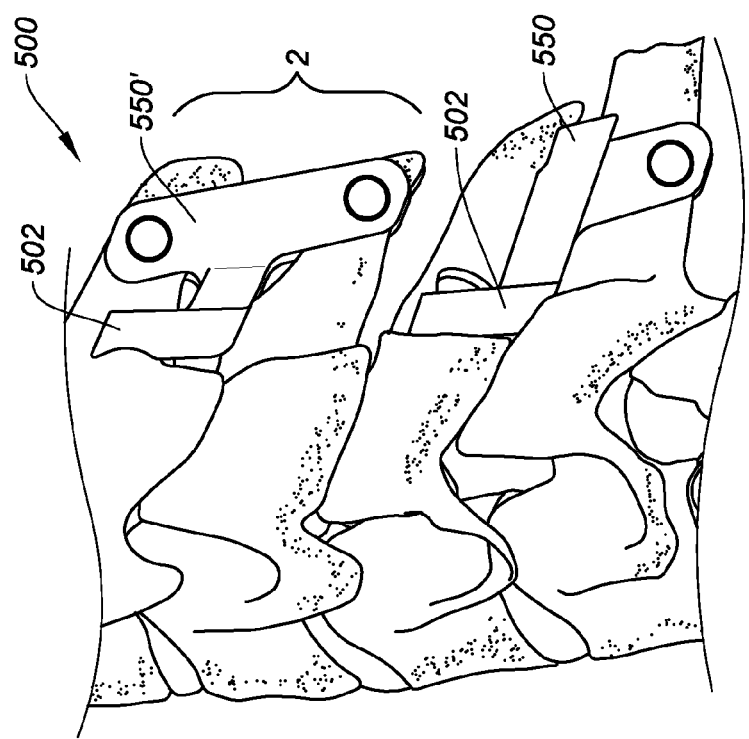
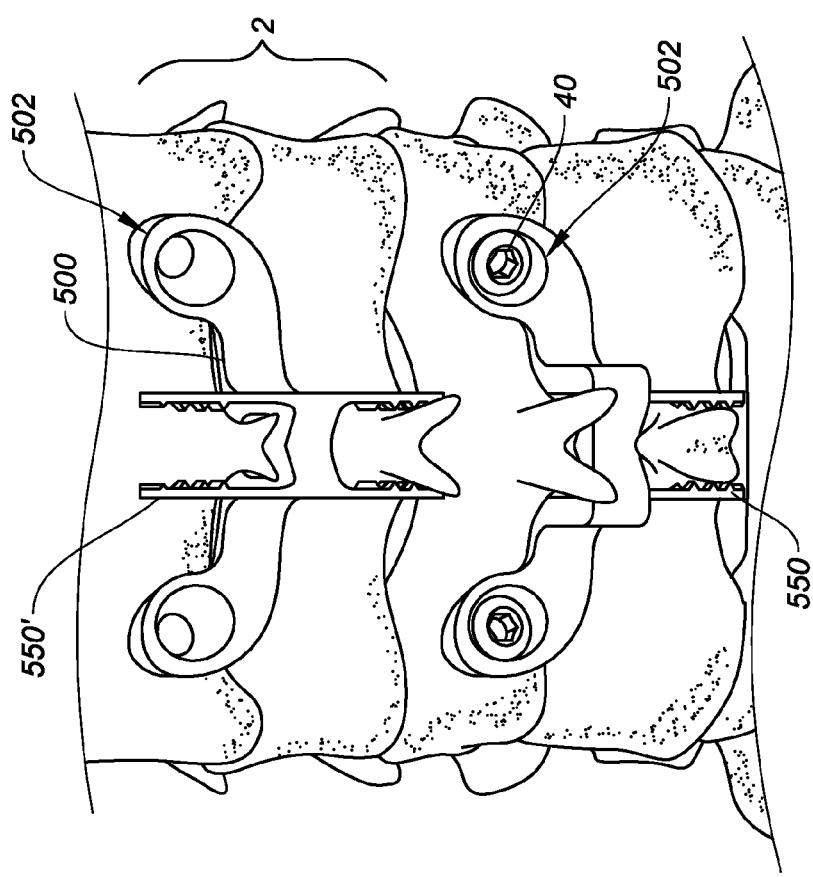
FIG. 15B
FIG. 15A

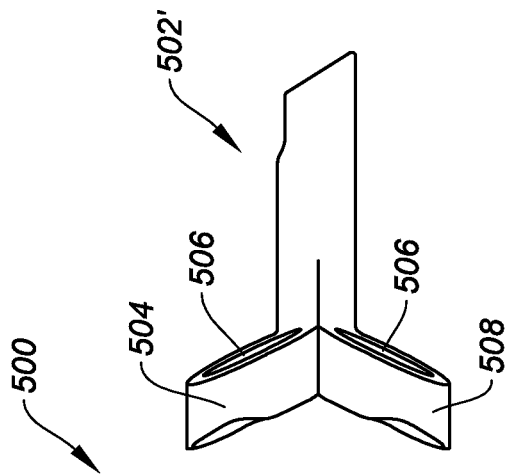
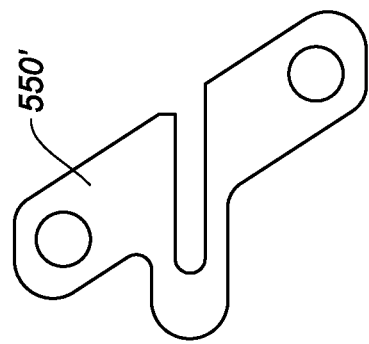
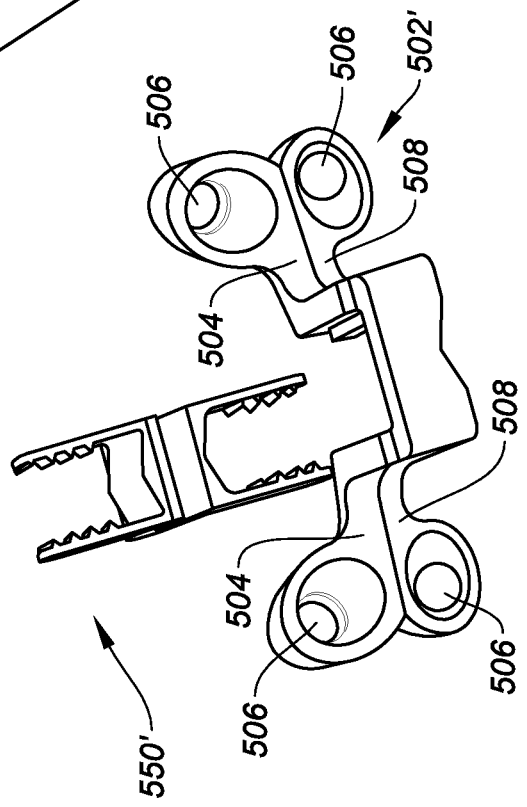
FIG. 16B
FIG. 16A

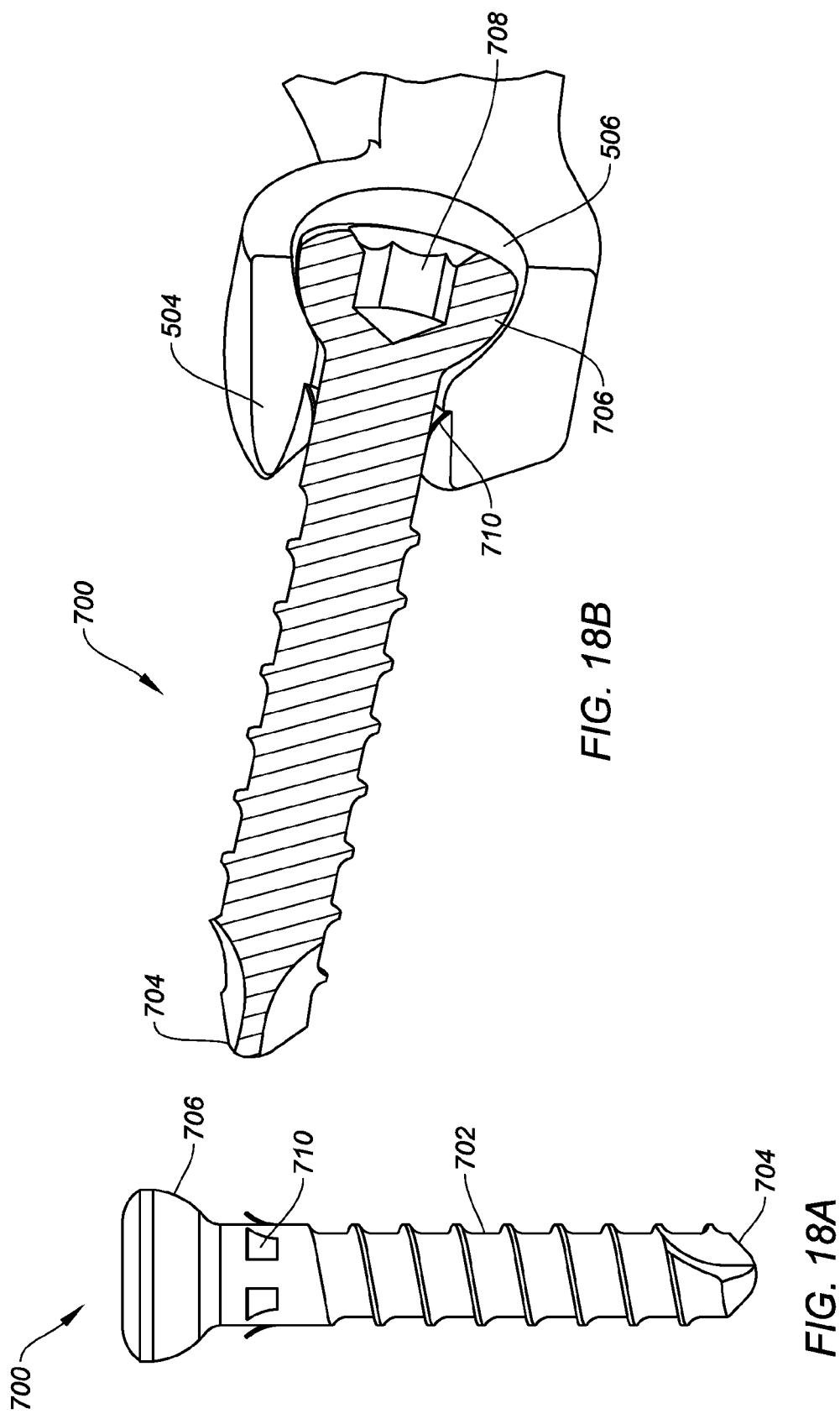

INTERLAMINAR, INTERSPINOUS STABILIZATION DEVICES FOR THE CERVICAL SPINE

CROSS-REFERENCE TO RELATED APPLICATIONS

This application claims priority under 35 U.S.C. § 119 based on U.S. Provisional Application No. 62/079,427, filed Nov. 13, 2014, the complete disclosure of which is incorporated herein by reference.

TECHNICAL FIELD

The present disclosure relates to devices and methods for treating spine instability, in particular the cervical spine, and includes interlaminar, interspinous stabilization devices and methods of using such devices for segmental stabilization of vertebrae of the cervical spine.

BACKGROUND

Spinal instability is often attributed to undesirable excessive motion between vertebrae and can cause significant pain and neurological deficits leading to significant morbidity and mortality. The instability may result from a number of causes, including abnormalities of the vertebrae, the intervertebral discs, the facet joints, and connective tissue around the spine. These abnormalities may arise from congenital abnormalities, diseases, disorders or defects of the spine from trauma or bone degradation, such as osteoarthritis, cancer, or degenerative disc disease. When the spine becomes unstable, the vertebral column becomes misaligned and may produce micromotion between adjacent vertebrae. Vertebral misalignment and micromotion may result in wear to the vertebral bone surfaces and ultimately generate severe pain. These conditions are often chronic and create progressive problems for the sufferer.

Known treatments for spinal instability can include long-term medical management, rehabilitation strategies, interventional (needle-based) approaches, or open surgery. Medical management is generally directed at controlling the symptoms, such as pain reduction, rather than correcting the underlying problem. For some patients, this may require chronic use of pain medications, which may alter patient mental state or cause other negative side effects. Rehabilitation strategies often focus on muscle strengthening and spinal alignment. Interventional approaches may include facet, disc, and/or nerve root injections of analgesics and/or anti-inflammatory medications. Surgical treatment typically includes neural decompression with and without spinal fusion. Procedures are often designed to decompress the nerve roots and/or spinal cord as well as restore vertebral alignment and orientation, replace or repair failing components (e.g. discs), and alleviate the pain.

Recently, a variety of interspinous stabilization devices have become available. These devices are typically implanted between the spinous processes of two or more adjacent vertebrae. By stabilizing the spinous processes in this way, significant stress may be taken off the intervertebral discs to prevent disease progression or to improve conditions such as spinal or neuroforaminal stenosis. In addition, vertebral motion may be controlled without severely altering the anatomy of the spine.

These devices, along with other interspinous stabilization systems, can be secured between adjacent spinous processes using a number of different mechanisms. For example, such devices can include sharp barbs or other surface projections that engage the bony surface of a spinous process. In addition, flexible ligaments or sutures can be placed around the implants and adjacent bone. In some cases, the devices may be rigidly attached to the spinous process using a bone screw or other suitable bone anchor to prevent the interspinous device from migrating or slipping out of position.

Fusion of the spine is a well-known and widely practiced medical procedure to alleviate symptoms and potential problems related to spinal instability such as severe back and/or neck pain due to misaligned, damaged or otherwise diseased spines. In many cases, spinal fusion is carried out by removing mobile interfaces (e.g. failing discs, facet joints, bone) followed by implantation of bone material and/or fusion-promoting adjuncts. Bony fusion can be significantly promoted by decreasing micromotion within the treated segments through orthosis or bracing. External orthosis (e.g. back brace) was the primary means of reducing micromotion and promoting fusion prior to the advent of internal spinal fixation systems. These systems initially employed wires to hold spinal segments firmly together. The wiring systems evolved to more rigid, durable implants including pedicle and lateral mass screws, rods, and intervertebral cages. These rigid spinal fixation systems are often designed to maintain or restore spinal alignment and spacing while enabling bone healing and fusion.

Where it is difficult to maneuver and insert rigid implantable device(s) due to the size limitations or delicate anatomical site (i.e., closeness to facet joints, nerves or spinal cord, for example) of the area to be implanted, it is desirable to provide an implant that inserts along the midline structures and may be converted from a flexible implant into a rigid one that can promote fusion as the spinal condition evolves.

It may be desirable in some situations, such as where the spinous process is damaged, weakened, brittle or insufficient in size to serve as a bearing surface, to provide an interspinous stabilization device that can support the spinal segment independent of the failing element(s). It is further desirable to provide an interspinous stabilization system that can be configured to provide either dynamic or rigid stability to the affected vertebral segment of the spinal column. For instance, it would be desirable to provide such a system whereby the dynamic stability allows for controlled motion of the adjacent vertebrae being affected for example following posterior cervical foraminotomy. It would be even more desirable to provide the same system having the ability to allow for rigid, fusion-promoting securement if so desired or needed. Further still, it would be desirable to provide a system that can provide the option of either dynamic or rigid stability at different levels of the vertebral segment, while also allowing for multi-level vertebral stabilization.

Whereas there are a number of options for the lumbar spine, very few such options exist for the cervical spine. Due to the limited space afforded the surgeon, and the biomechanical considerations of the highly-mobile cervical spine, the much desired option of a dynamic stabilization device is rarely available. Even more desirable are convertible devices that allow the option of either dynamic or rigid fixation at the spinal segment of the cervical spine to be treated. Accordingly, it is desirable to provide dynamic, rigid, and convertible dynamic to rigid devices and methods of using such devices for interlaminar, interspinous stabilization of the cervical spine.

SUMMARY

The present disclosure provides dynamic, rigid, and convertible dynamic-to-rigid devices and methods of using such devices to treat spinal instability conditions of the cervical spine. The devices may include an interspinous, interlaminar stabilization device configured for interlaminar placement between the spinous processes of adjacent cervical vertebrae and optionally secured to the lamina using bone screws or crimped or rigidly fixed to the spinous process. Multiple devices may be used to enable treatment of multiple levels at the same time.

In one aspect of the present disclosure, interlaminar, interspinous spinal stabilization devices configured for rigid fixation are provided. These devices may comprise a unitary body having a contour suitable for placement between adjacent cervical vertebrae. In one embodiment, the unitary body may include screw holes to accommodate bone screws such as lateral mass screws. In another embodiment, the body may include brackets for receiving a spinous process of the cervical spine. These brackets may be crimped onto the spinous process. Alternatively, or in addition to the crimping, the brackets may include through-holes for receiving a rivet therethrough. In another embodiment, the body may include extended wings and/or brackets. These devices are configured for rigid fixation of the spinal segment, thereby enabling fusion at that level.

In another aspect of the present disclosure, interlaminar, interspinous spinal stabilization devices configured for dynamic fixation are provided. These devices may comprise a unitary body having a contour suitable for placement between adjacent cervical vertebrae. In one embodiment, the unitary body may include upper and lower plates connected by a flexible hinge or midsection. The unitary body may include one or more pair of brackets for receiving a spinous process of the cervical spine. These brackets may be crimped onto the spinous process. Alternatively, or in addition to the crimping, the brackets may include through-holes for receiving a rivet therethrough. In still another embodiment, the body may include straps for securing around the spinous process. These devices are configured for dynamic fixation of the spinal segment.

In still another aspect of the present disclosure, modular, two-part interlaminar, interspinous spinal stabilization devices are provided. These two-part devices are configured for conversion from a dynamic-to-rigid segmental stabilization of the cervical spine. In one embodiment, a dynamic fixation device may be provided with screw holes for fixation with bone screws. The dynamic fixation device may include an opening for receiving a complementary rigid fixation device. The rigid fixation device may act to block the dynamic fixation device, thereby hindering movement and promoting fusion. In one embodiment, the rigid fixation device may comprise one or more brackets for receiving a spinous process. These brackets may be crimped onto the spinous process. Alternatively, or in addition to the crimping, the brackets may include through-holes for receiving a rivet therethrough.

In further aspect of the present disclosure, various locking screws and mechanisms are provided for use with the devices of the present disclosure. In one embodiment, a retaining plate or locking plate may be provided for use with the devices to prevent backout of screws from the screw holes. In another embodiment, the screw may be provided with self-cutting threads to embed the screw into the screw hole during insertion, thereby preventing backout. In still another embodiment, the screw may be provided with spring tongues to embed the screw into the screw hole during insertion, thereby preventing backout.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 1A shows a top-down view of an exemplary embodiment of an interlaminar, interspinous spinal stabilization device of the present disclosure.

FIG. 1B shows an exploded perspective view of the device of FIG. 1A along with an optional retaining or locking plate of the present disclosure.

FIG. 5A shows a front view of still another exemplary embodiment of an interlaminar, interspinous spinal stabilization device of the present disclosure.

FIG. 5B shows a perspective view of the device of FIG. 5A.

FIGS. 7A and 7B show perspective views of the device of FIGS. 5A and 5B in use in a cervical spine.

FIGS. 9A and 9B show perspective views of the device of FIGS. 8A and 8B in use in a cervical spine.

FIG. 10A shows a perspective view of even still another exemplary embodiment of an interlaminar, interspinous spinal stabilization device of the present disclosure.

FIG. 10B shows the device of FIG. 10A in use with optional bone screws and optional rivet.

FIG. 11A shows a perspective view of yet another exemplary embodiment of an interlaminar, interspinous spinal stabilization device of the present disclosure.

FIG. 11B shows the device of FIG. 11A in use with optional rivet.

FIG. 12A shows a perspective view of an exemplary embodiment of a modular, two-part interlaminar, interspinous spinal stabilization device of the present disclosure.

FIG. 12B shows a top-down view of the device of FIG. 12A.

FIG. 13A shows an exploded view of another exemplary embodiment of a modular, two-part interlaminar, interspinous spinal stabilization device of the present disclosure.

FIG. 13B shows a top-down view of the fully assembled device of FIG. 13A.

FIGS. 15A and 15B show perspective views of the device of FIG. 14 in use in a cervical spine.

FIGS. 16A-16C show perspective exploded views of even still another exemplary embodiment of a modular, two-part interlaminar, interspinous spinal stabilization device of the present disclosure.

FIG. 18A shows a perspective view of an exemplary embodiment of a bone screw suitable for use with the interlaminar, interspinous spinal stabilization devices of the present disclosure.

FIG. 18B shows a partial cross-sectional view of the bone screw of FIG. 18A in use with a device of the present disclosure.

DETAILED DESCRIPTION

Figure 2A:
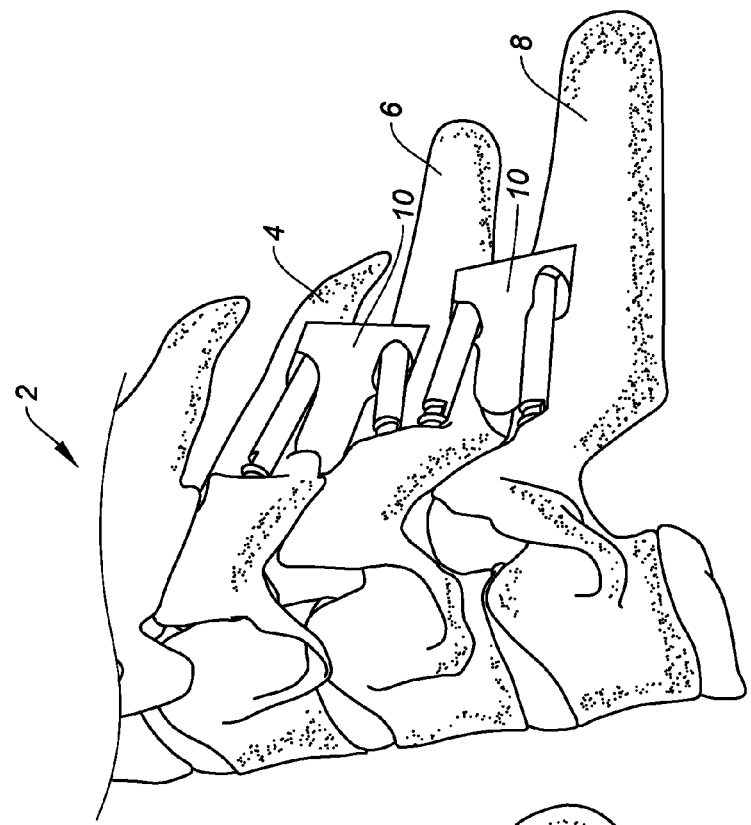
FIGS. 2A-2C show perspective views of the device of FIG. 1A in use in a cervical spine.

FIG. 1A illustrates an exemplary embodiment of an interlaminar, interspinous spinal stabilization device 10 of the present disclosure. The device 10 may comprise a main body 12 having an upper surface 14, a lower surface 16, an anterior portion 18, and a posterior portion 20. The main body 12 may be formed as a solid body, and as such, the upper and lower surfaces 14, 16 and the anterior and posterior portions 18, 20 may be interconnected, as illustrated. The main body 12 itself may also be shaped to conform to the anatomy of the spine, and in particular, the cervical spine 2. For instance, the posterior portion 20 may be slightly curved, as shown, as can be the sides 26 of the main body 12.

Figure 2B:
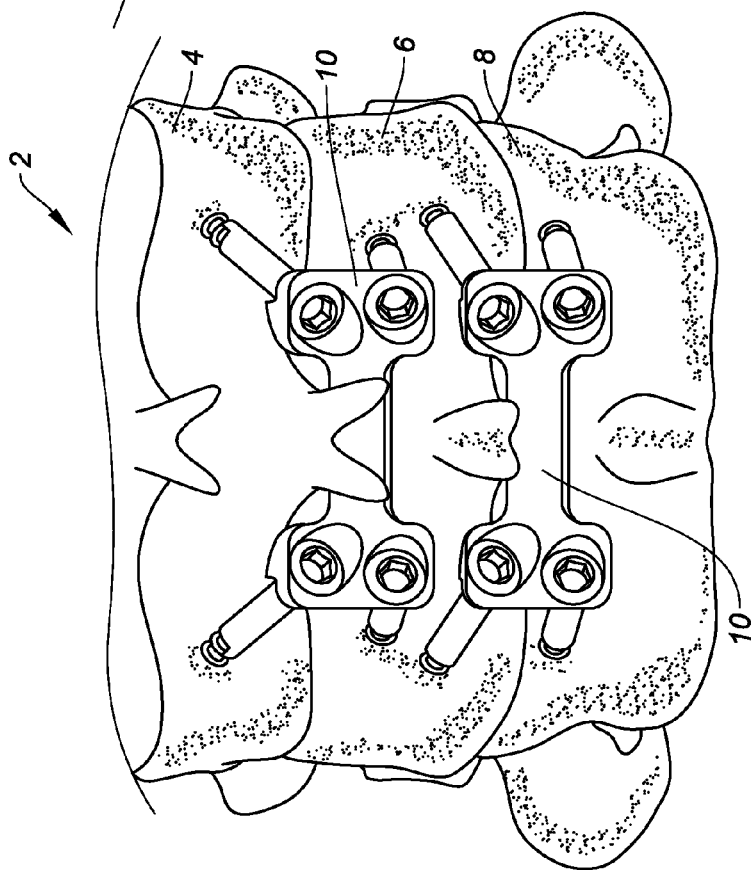
Figure 2C:
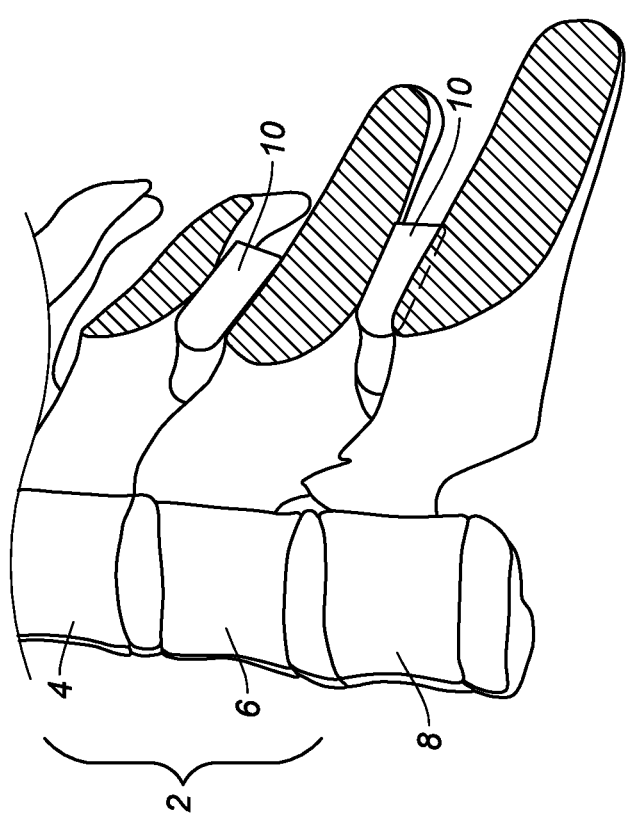

As further illustrated, the four corners 22 of the main body 12 at the anterior portion 18 can be enlarged to accommodate screw holes 24. The screw holes 24 may be angled to allow the insertion of screws 40 through the holes and towards the upper or lower vertebrae 4, 6, 8 of the cervical spine 2, as shown in FIGS. 2A to 2C. In one embodiment, these screws 40 may diverge and extend upwardly or downwardly. These screws 40 may be, for example, lateral mass screws and may include an elongated shaft 42 with a threaded tip 44 at one end and a screw head 46 at an opposite end. Such use of lateral mass screws 40 along with the implantable device 10 would enable a rigid, secure fixation of the device 10 in between the cervical vertebrae and consequently stabilize that vertebral segment of the spine 2 being treated.

The implantable devices 10 of FIGS. 1A and 1B may be contoured to allow ease of insertion in between the vertebrae, such as for example, by providing a main body 12 having a wedge shape. For instance, the sides 26 and posterior portion 20 may be tapered or narrowed to provide a leading edge. Additionally, the main body 12 may have a low profile to allow stacking of devices 10 at multiple levels. This stacking is illustrated in FIGS. 2A to 2C in which multiple devices 10 may be used in adjacent levels of the cervical spine 2, without abutting one another or crowding the area. The contours of the main body 12 enable the device 10 to have a closely matched fit within the interspinous space of the cervical spine 2. Thus, when in use, the device 10 provides sufficient interlaminar support of the cervical vertebrae 4, 6, 8, as shown in FIGS. 2B and 2C. Accordingly, the device 10 may be appropriately considered an interspinous, interlaminar spinal stabilization device 10 for the cervical spine.

FIG. 1B illustrates the interlaminar, interspinous spinal stabilization device 10 of FIG. 1A with an optional retaining or locking plate 50. Retaining plates, also known as locking plates, 50 are known in the industry for use in blocking the opening of screw holes 24 and the associated screw heads 46 within these screw holes 24 to prevent undesired screw backout, or the loosening of the screws out of the device 10, over time and with repeated micromotion. As shown in FIG. 1B, an exemplary embodiment of a locking plate 50 may be provided along with the interlaminar, interspinous spinal stabilization device 10 of FIG. 1A. The locking plate 50 may have a similar, complementary shape as the anterior portion of device 10, with a narrowed midsection flanked by enlarged arms 52. The plate 50 may include a screw hole 54 for insertion of a fixation screw (not shown) into a receiving hole 32 in the anterior portion 18 of the device 10, to securely lock the locking plate 50 onto the main body 12. Once fixed to the main body 12, the locking plate 50 should rest firmly against the anterior portion, while the arms 52 should cover or block at least a portion of the screw holes 24 and screw heads 46.

Figure 3A:
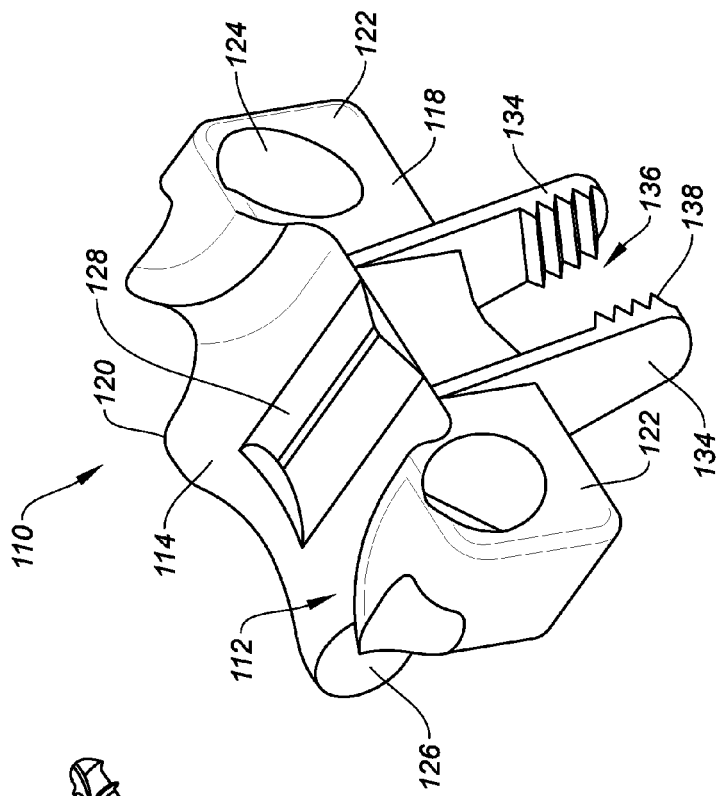
FIG. 3A shows a perspective view of another exemplary embodiment of an interlaminar, interspinous spinal stabilization device of the present disclosure.
Figure 3B:
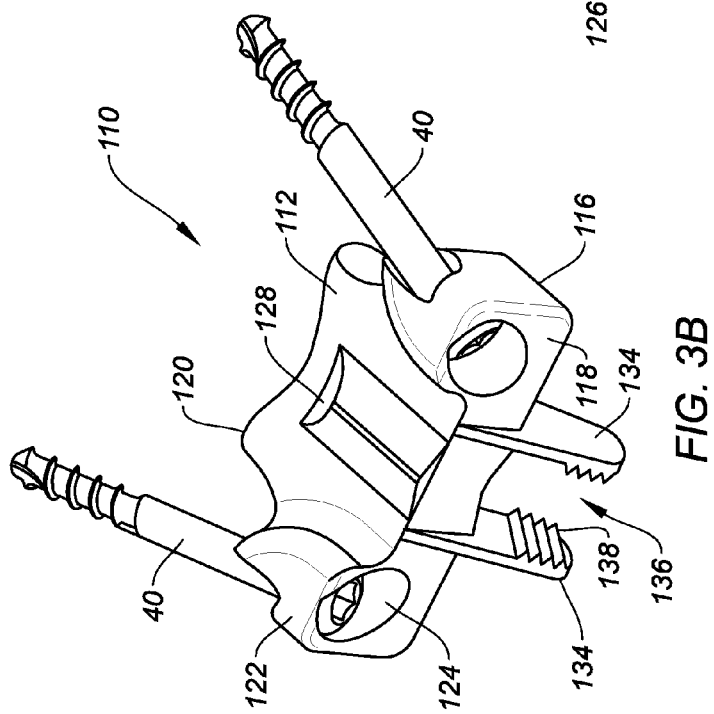
FIG. 3B shows the device of FIG. 3A in use with bone screws.
Figure 4B:
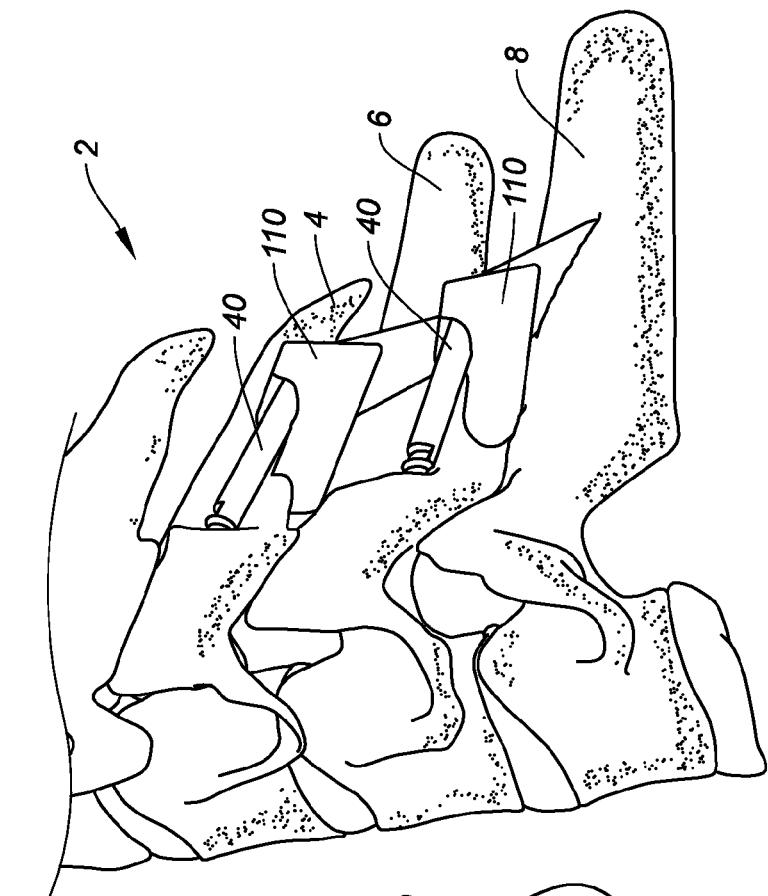
FIGS. 4A and 4B show perspective views of the device of FIG. 3B in use in a cervical spine.
Figure 4A:
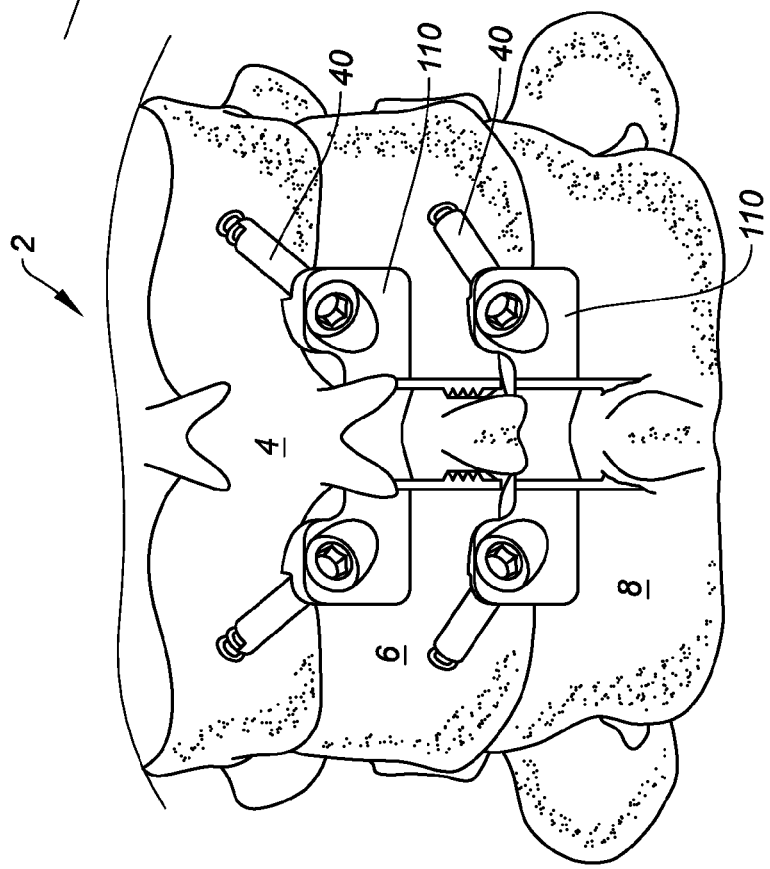

FIGS. 3A and 3B illustrate another exemplary embodiment of an interspinous, interlaminar spinal stabilization device 110 of the present disclosure, while FIGS. 4A and 4B illustrate the device 110 in situ in a cervical spine 2. The device 110 of FIGS. 3A and 3B share similar features to the device 10 of FIGS. 1A and 1B. As such, these similar features are designated by the same reference number following the prefix "1". Like device 10, device 110 may comprise a main body 112 having an upper surface 114, a lower surface 116, an anterior portion 118, and a posterior portion 120. The main body 112 may be formed as a solid body, and as such, the upper and lower surfaces 114, 116 and the anterior and posterior portions 118, 120 may be interconnected, as illustrated. The main body 112 may also be shaped to conform to the anatomy of the spine, and in particular, the cervical spine 2. For instance, the posterior portion 120 may be slightly curved, as can be the sides 126 of the main body 112. Such curvature enables the form-fitting adherence of the device 110 to the anatomical region of the intervertebral space of the cervical spine 2, as previously described above.

Also like device 10, the two corners 122 of the main body 112 at the anterior portion 118 can be enlarged to accommodate screw holes 124. The screw holes 124 may be angled to allow the insertion of screws 40 such as those previously described through the holes and towards the upper or lower vertebrae 4, 6, 8 of the cervical spine 2, as shown in FIGS. 4A and 4B. In one embodiment, these screws 40 may diverge and extend upwardly or downwardly. Use of the screws 40 would enable a rigid, secure fixation of the device 110 in between the cervical vertebrae and consequently stabilize that vertebral segment of the spine 2.

In addition, device 110 may further include a surface modification such as a protrusion or fin 128 on the upper surface 114 of the main body 112, as illustrated. This protrusion or fin 128 may further enhance stabilization and anchorage within the interspinous space. In addition, device 110 may be configured to have a pair of brackets 134 extending from the lower surface 116 of the main body 112. These brackets 134 may collectively form a stirrup, or bone-receiving region 136. As illustrated in FIGS. 4A and 4B, these brackets 134 allow the device 110 to receive a spinous process of the lower vertebra. The brackets 134 may be configured to be malleable, and allow crimping onto the spinous process. Teeth, spikes, barbs, ridges, or other similarly sharp bone-piercing protrusions or surface roughening features 138 may be provided on the brackets 134 to further enhance bone contact with the spinous process.

Like device 10 above, the interlaminar, interspinous spinal stabilization device 110 of FIGS. 3A and 3B may utilize one or two different types of fixation mechanisms: screw fixation, such as for example with lateral mass screws 40, may be utilized for securing the device 110 to the upper vertebra, while crimping to the spinous process of the lower vertebra may also be utilized. The device 110 is configured such that either one or both mechanisms may be implemented, without affecting the other mechanism. And similar to device 10, the present device 110 also allows stacking or multiple devices 110 to be used at one time at different levels of the cervical spine 2. FIGS. 4A and 4B illustrate the use of the devices 110 whereby one level utilizes screw fixation while the other level utilizes crimping.

Turning now to FIGS. 5A, 5B, 6, 7A, 7B, 8A, 8B, 9A, and 9B, the present disclosure also provides exemplary embodiments of interlaminar, interspinous spinal stabilization devices 200 that are flexible and allow some motion of the cervical vertebrae while simultaneously stabilizing the vertebral level. FIGS. 5A and 5B illustrate one such exemplary embodiment. Device 200 as shown in FIGS. 5A and 5B may comprise an upper plate 202 and a lower plate 204 connected by a flexible midsection 206, allowing the plates 202, 204 to move relative to one another. The plates 202, 204 create an open free end 208, as illustrated. The device 200 may be configured to nest securely in between the cervical vertebrae, as illustrated in FIGS. 7A and 7B.

Due to the unique anatomy of the cervical spine 2, the upper plate 202 may be shorter in length than the lower plate 204, as can be seen in FIGS. 5B and 7B. In addition, the plates 202, 204 may also be contoured, or curved, in order to matingly fit and interlaminarly support the cervical vertebra at that level. The upper plate 202 may further include a surface modification such as a protrusion or fin 228, as illustrated. This protrusion or fin 228 may further enhance stabilization and anchorage within the interspinous space, similar to previously described protrusion or fin 128 above.

Brackets 214 may be provided on the upper and lower plates 202, 204. Each pair of brackets 214 may create a stirrup, or bone-receiving area 216, for receiving a spinous process, as can be seen in FIG. 7A. The brackets 214 may be malleable, to allow crimping onto the spinous process, as previously described with bracket 134 of device 110. Additionally, brackets 214 may include teeth, spikes, barbs, ridges, or other similarly sharp bone-piercing protrusions or surface roughening features 218 to further enhance bone contact with the spinous process. These brackets 214 may be angled relative to the upper and lower surfaces 202, 204, as illustrated in FIGS. 5B and 7B, in order to conform to the unique anatomy of the cervical spine, and allow stacking or multi-level stabilization, as shown in FIGS. 7A and 7B.

Figure 6:
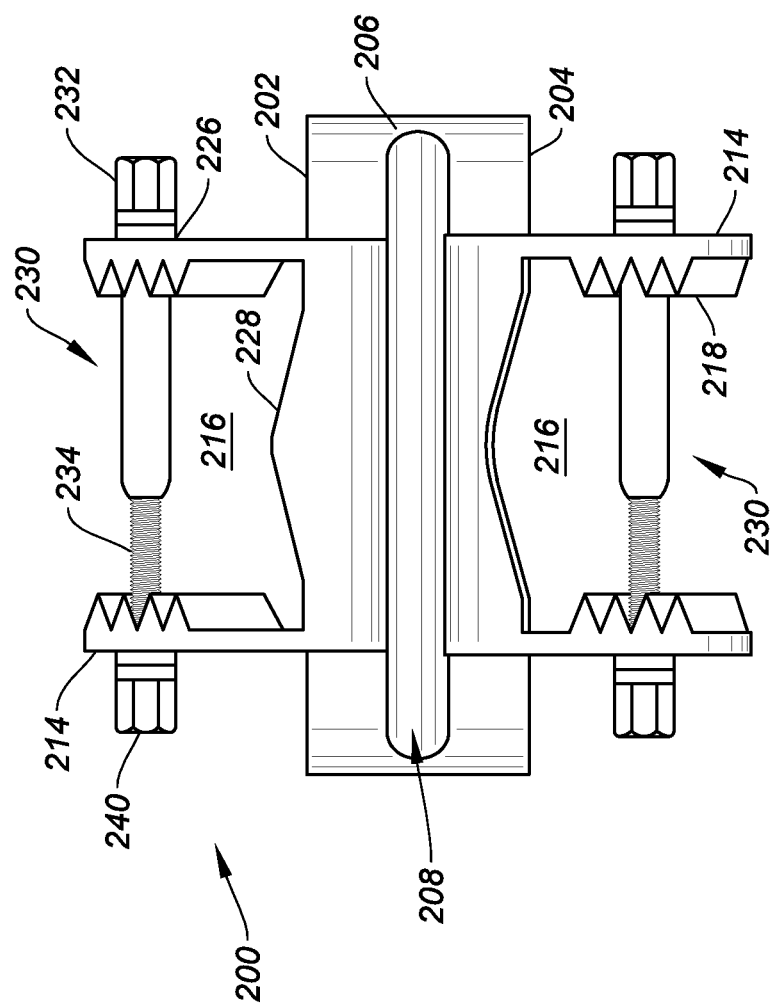
FIG. 6 shows a front view of the device of FIGS. 5A and 5B with optional rivets.

FIG. 6 illustrates another exemplary embodiment in which interspinous, interlaminar spinal stabilization device 200 may optionally utilize a fixation element through the brackets 214. As shown, the device 200 of the present disclosure may be provided with through-holes 226 at each of the brackets 214 for receiving a rivet 230 therethrough. As used herein, it is to be understood that the term rivet is intended to broadly encompass a nut and bolt assembly, without limitation. The rivet 230 may comprise a threaded bolt 232 that threadingly engages a threaded nut 240 at threaded end 234. Either one or both of the pair of brackets 214 of the device 200 may utilize this additional fixation mechanism.

It is contemplated that the user may elect to crimp the brackets first 214, then place the rivet 230 through the brackets 214 to secure them onto the spinous process, or merely use the rivet 230 without first crimping, as the rivet 230 would effectively move the brackets 214 together in a crimping manner during installation. Furthermore, the user has the option of utilizing crimping and/or rivet installation in either one or both of the pair of brackets 214. Accordingly, it is possible to crimp at the upper level, and use a rivet 230 at the lower level, or vice versa, without affecting the stability of the device 200. Such flexibility enables the user to customize the level of rigidity, fixation, and flexibility of the device at a single level. For example, while not shown, it is contemplated that any one or more of the devices 200 of FIGS. 7A and 7B may also include a rivet 230 through the pair of brackets 214 of the upper or the lower plates 202, 204, as desired.

Figure 8B:
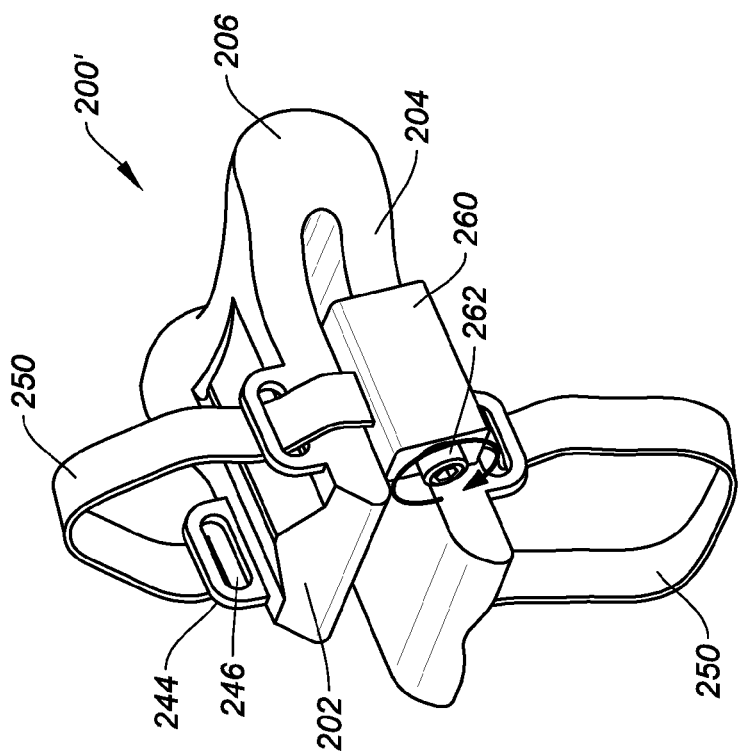
FIGS. 8A and 8B show perspective views of yet another exemplary embodiment of an interlaminar, interspinous spinal stabilization device of the present disclosure.
Figure 8A:
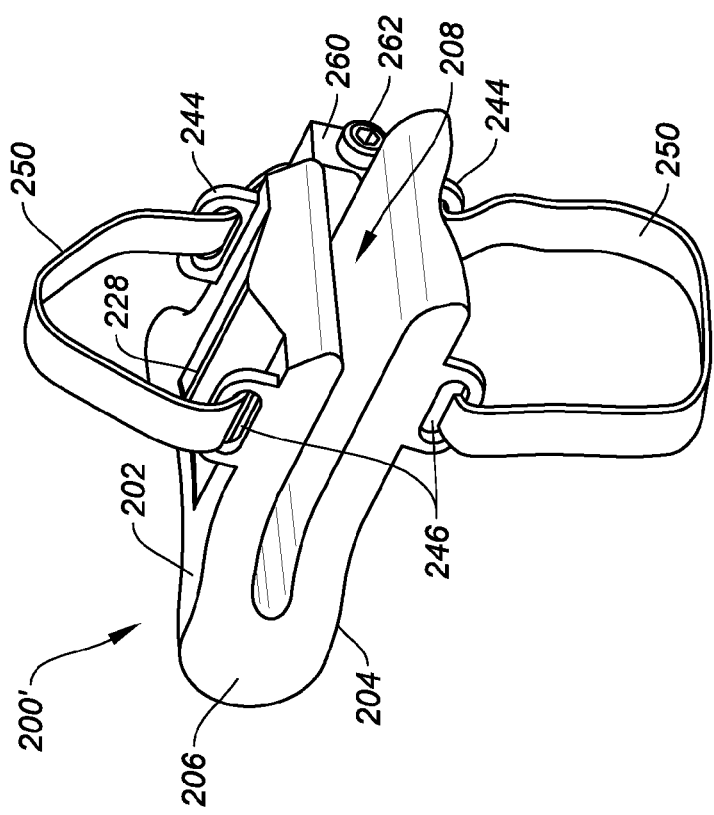

FIGS. 8A and 8B illustrate yet another exemplary embodiment of the interspinous, interlaminar spinal stabilization device 200' of the present disclosure. The device 200' shares all of the same features of device 200 of FIGS. 5A and 5B, with the exception that, in this embodiment, the brackets 214 are replaced with bars 244. These bars 244 may include a slot 246 for receiving a fastening element such as a tie, belt, or strap 250, such as illustrated. The straps 250 may be configured to securely wrap around the upper or lower spinous processes of the level of the cervical spine being stabilized. As shown, the straps 250 may be connected to a housing unit 260 that allows length-wise adjustment by a mechanism such as a rotating knob or dial 262. In one embodiment, the adjustment mechanism may comprise a screw that, when rotated, tightens the straps 250 around the spinous process. This housing unit 260 may be located at the side of the device 200'. Use of the strap 250 would thus enable fixation without the need to drill a hole through the spinous process. FIGS. 9A and 9B illustrate the use of this embodiment in situ, at a single level. Of course, it is contemplated that multiple devices 200' may be stacked and therefore multiple levels may be stabilized at the same time, as previously described.

FIGS. 10A and 10B illustrate even still another exemplary embodiment of the interspinous, interlaminar spinal stabilization device 300 of the present disclosure. The device 300 may comprise a main body 302 having two different pairs of extensions for attachment to bone: a pair of wings or arms 304 that extend upwardly from the main body 302, and a pair of brackets 314 extending downwardly from the main body 302. Each of these extensions will be described in greater detail now.

As shown, wings or arms 304 may extend from the main body 302 in an upwardly direction. The ends of the wings or arms 304 may include screw holes 306 for receiving a bone screw such as, for example, the lateral mass screws 40 previously described. The screw holes 306 may be angled to allow the screws 40 to be inserted into the body of the vertebra of the upper level where stabilization is taking place.

A pair of brackets 314 may extend downwardly from the main body 302 to create a stirrup or bone-receiving area 316 for receiving a spinous process. The brackets 314 may further include teeth, barbs, spikes, ridges, or other similarly sharp bone-piercing protrusions or surface roughening features 318 to further enhance bone contact with the spinous process. These brackets 314 may be angled relative to the main body 302, in order to conform to the unique anatomy of the cervical spine, and allow stacking or multi-level stabilization, as previously described and shown. Also similar to the devices previously described, the brackets 314 may optionally utilize a fixation element through the brackets 314. As shown, the device 300 of the present disclosure may be provided with through-holes 326 at each of the brackets 314 for receiving a rivet 230 therethrough. The rivet 230 may comprise a threaded bolt 232 that threadingly engages a threaded nut 240, similar to the rivet 230 previously described.

The main body 302 may further include a central opening 310 which may be used to hold a fusion enhancing material or therapeutic agent, such as for example, bone substitute material, bone morphogenic protein, bone graft material including demineralized bone matrix, bone chips, autograft, allograft, xenograft, medical agents, stem cells, proteins, or other biological agents that promote bone fusion or provide therapeutic benefits, including antibiotics or antimicrobial agents and the like. The main body 302 may additionally include a surface modification such as a protrusion or fin 328, as illustrated. This protrusion or fin 328 may further enhance stabilization and anchorage within the interspinous space, similar to previously described protrusion or fin 128, 228 above.

FIGS. 11A and 11B show a variation of device 300' in which all of the features of device 300 are present, along with an additional pair of brackets 314. As illustrated, the device 300' provides yet an additional extension comprising an upwardly extending pair of brackets 314. The upwardly extending pair of brackets 314 is identical to those extending downwardly, and are angled and shaped to match the anatomy of the cervical spine 2. FIG. 11B shows the device 300' in use with a rivet 230 through the upwardly extending brackets 314. It is understood, of course, that the rivet 230 may be utilized by the lower brackets 314, or both upper and lower brackets 314, with optional lateral mass screws 40 extending through the wings 304. At the same time, the user may optionally crimp the brackets 314 in addition to, or instead of, using the rivet 230. Accordingly, this type of unitary body 302 provides several different rigid fixation options at different locations, thereby promoting fusion.

FIGS. 12A, 12B, 13A, 13B, 14, 15A, 15B, and 16A-16D show various exemplary embodiments of a modular, two-part interspinous spinal stabilization device of the present disclosure. Turning now to FIGS. 12A and 12B, a two-part modular design for an interlaminar, interspinous spinal stabilization device 400 is illustrated. The device 400 may comprise a main frame 402 having a sleeve-receiving opening 410 for receiving a sleeve or insert 450. The main frame 402 may further include upwardly extending arms or wings 404, similar to the wings or arms 304 previously described above. The wings or arms 404 may include angled screw holes 406 similar to the screw holes 306 previously described above.

Within the main frame 402 is an insert or sleeve 450 comprising a main body 452. A pair of brackets 454 extends upwardly from the main body 452, while another pair of brackets 454 extends downwardly from the main body 452 in a fashion similar to that shown in FIGS. 11A and 11B of device 300'. Like device 300', the pair of brackets 454 creates a stirrup or bone-receiving area 456 for receiving a spinous process. The brackets 454 may further include teeth, spikes, barbs, ridges, or other similarly sharp bone-piercing protrusions or surface roughening features 458 to further enhance bone contact with the spinous process. These brackets 454 may be angled relative to the main body 452, in order to conform to the unique anatomy of the cervical spine, and allow stacking or multi-level stabilization, as previously described and shown. Also similar to the devices previously described, the brackets 454 may optionally utilize a fixation element through the brackets 454. Accordingly, the brackets 454 may be provided with through-holes 464 for receiving a rivet 230 therethrough. The rivet 230 may comprise a threaded bolt 232 that threadingly engages a threaded nut 240, similar to the rivet 230 previously described.

The main body 452 may further include a central opening 460 which may be used to hold a bone graft or other fusion enhancing material. The main body 452 may additionally include a surface modification such as a protrusion or fin 462, as illustrated. This protrusion or fin 462 may further enhance stabilization and anchorage within the interspinous space, similar to previously described protrusion or fin 128, 228, 328 above.

Although not shown, it is contemplated that bone screws such as, for example, lateral mass screws 40 may be used to fix the wings 404 of the main frame 402 to a vertebra. Optional rivets 230 may be used for fixing either or both of the pair of brackets 454 to a spinous process. Additionally, each of the pair of brackets may be configured to be crimped onto the spinous process, either instead of, or in addition to, the use of the rivets for rigid fixation.

In one embodiment, the two components of the device 400 may comprise different materials for different properties. For example, the main frame 402 may be formed of a polyetheretherketone (PEEK) material to facilitate fixation with lateral mass screws 40, while the sleeve or insert 450 may be formed of a metal such as, for example, titanium to allow optional crimping and/or fixation with a rivet 230.

FIGS. 13A and 13B illustrate still another exemplary embodiment of a two-part modular interlaminar, interspinous spinal stabilization device 500. The device 500 shares similar features to device 400 previously described, and may comprise a main frame 502 having an insert-receiving slot 510 for receiving an insert 550. The main frame 502 may further include upwardly extending arms or wings 504, similar to the wings or arms 304, 404 previously described above. The wings or arms 504 may include angled screw holes 506 similar to the screw holes 306, 406 previously described above for use with a bone screw such as, for example, the lateral mass screws 40 previously described. However, unlike the opening 410 of device 400, the insert-receiving slot 510 of device 500 is partially open and contains a rail 512 for sliding engagement with the insert 550, as shown by the arrow in FIG. 13A.

The insert 550 may comprise a main body 552, and a pair of brackets 554 extending downwardly from the main body 552 in a fashion similar to that shown in FIGS. 11A and 11B of device 300'. Like device 300', the pair of brackets 554 creates a stirrup or bone-receiving area 556 for receiving a spinous process. The brackets 554 may further include teeth, spikes, barbs, ridges, or other similarly sharp bone-piercing protrusions or surface roughening features 558 to further enhance bone contact with the spinous process. These brackets 554 may be angled relative to the main body 552, in order to conform to the unique anatomy of the cervical spine, and allow stacking or multi-level stabilization, as previously described and shown. Also similar to the devices previously described, the brackets 554 may optionally utilize a fixation element through the brackets 554. Accordingly, the brackets 554 may be provided with through-holes 564 for receiving a rivet 230 therethrough. The rivet 230 may comprise a threaded bolt 232 that threadingly engages a threaded nut 240, similar to the rivet 230 previously described.

The main body 552 may further include a central opening 560 which may be used to hold a fusion enhancing material or therapeutic agent such as described above. The main body 552 may additionally include a surface modification such as a protrusion or fin 562, as illustrated. This protrusion or fin 562 may further enhance stabilization and anchorage within the interspinous space, similar to previously described protrusion or fin 128, 228, 328, 462 above. In addition, the main body 552 may include a groove 566 that allows the body 552 to be slidingly inserted into the insert-receiving opening 510 of the main frame 502 along the rails 512. FIG. 13B shows a fully assembled device 500 in which the insert 550 is nested securely within the frame 502 of device 500.

Although not shown, it is contemplated that bone screws such as, for example, lateral mass screws 40 may be used to fix the wings 504 of the main frame 502 to a vertebra. Optional rivet 230 may be used for fixing the pair of brackets 554 to a spinous process. Additionally, the pair of brackets may be configured to be crimped onto the spinous process, either instead of, or in addition to, the use of the rivet for rigid fixation.

As previously described for device 400, the two components of the device 500 may comprise different materials for different properties. For example, the main frame 502 may be formed of a polyetheretherketone (PEEK) material to facilitate fixation with lateral mass screws 40, while the insert 550 may be formed of a metal such as, for example, titanium to allow optional crimping and/or fixation with a rivet 230.

Figure 14:
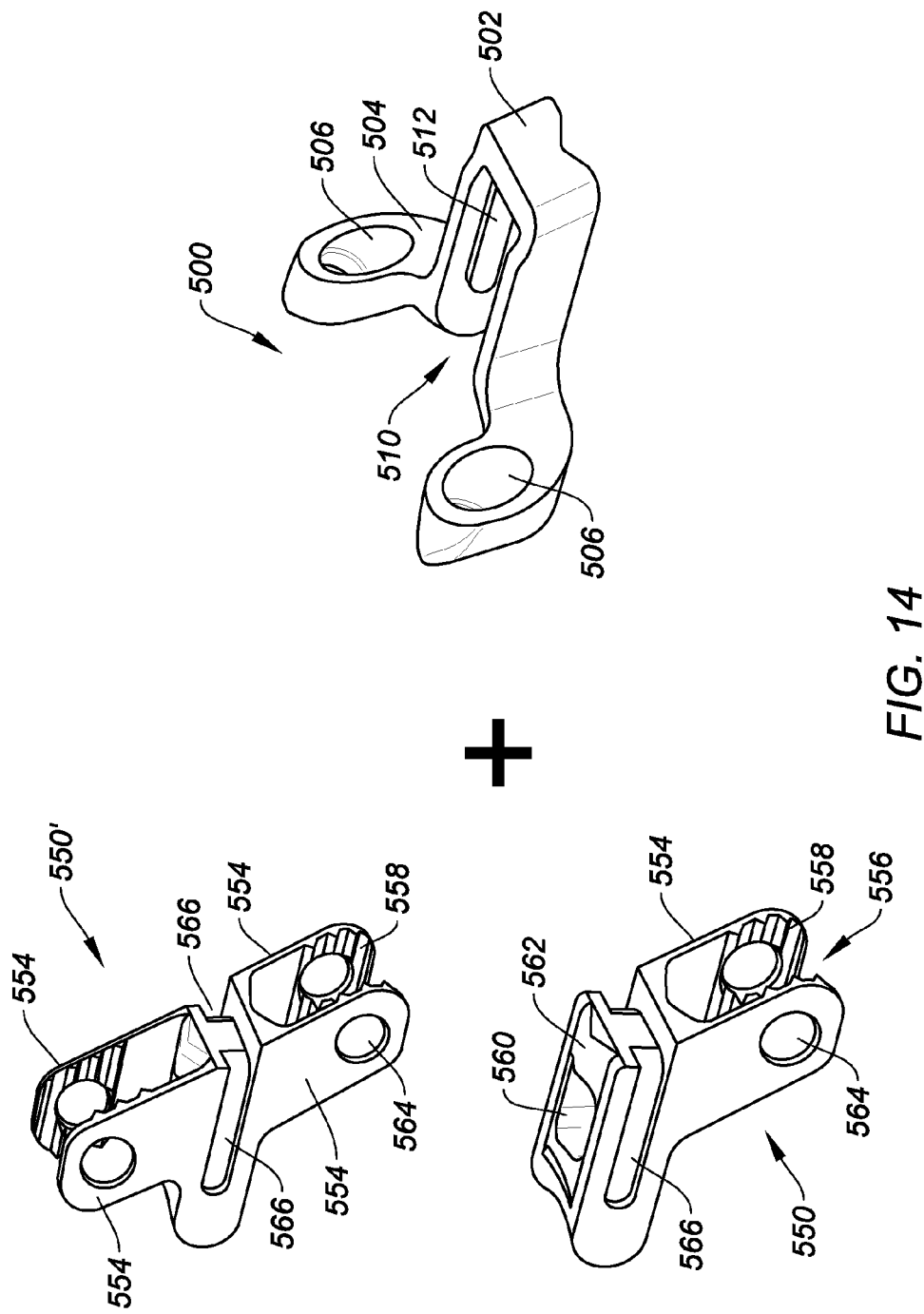
FIG. 14 shows an exploded view of still other exemplary embodiment of a modular, two-part interlaminar, interspinous spinal stabilization device of the present disclosure.
Figure 16C:
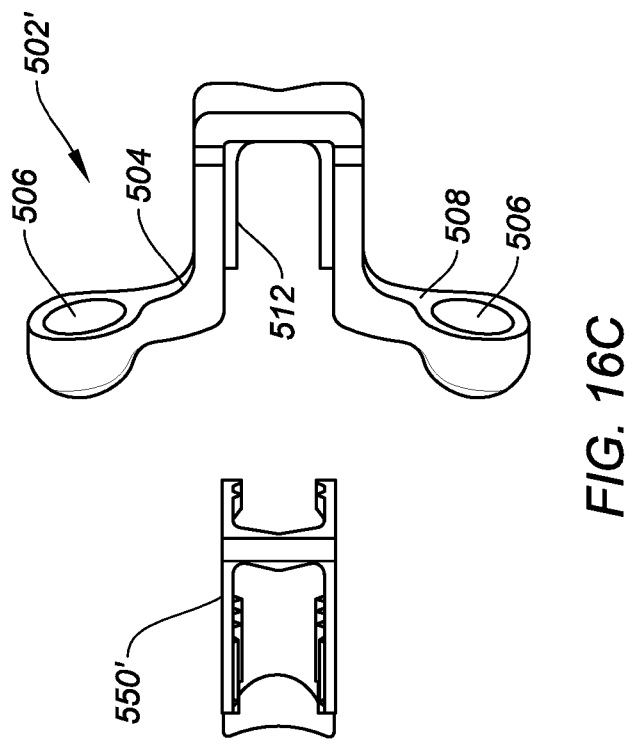
Figure 16D:
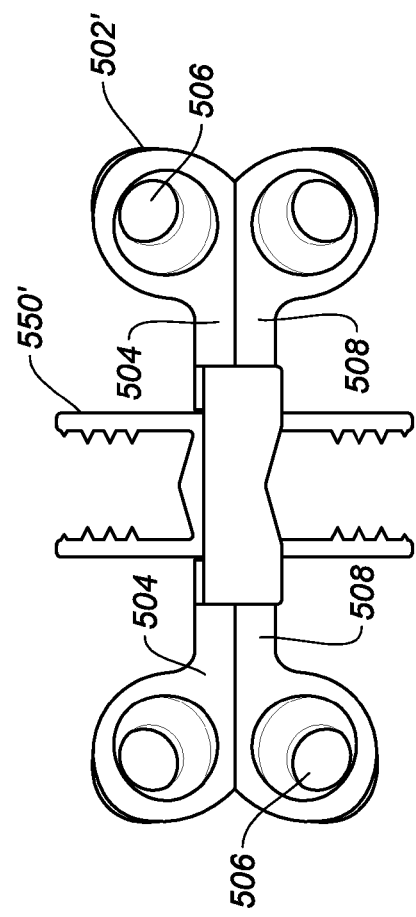
FIG. 16D shows a front view of the fully assembled device of FIGS. 16A-16C.

The main frame 502 as well as the insert 550 may be provided in various other forms to provide ultimate flexibility regarding the amount of fixation to bone that can be provided. For instance, FIG. 14 shows the main frame 502 of device 500 but with the option of an insert 550' instead of insert 550. Insert 550' is similar to insert 550, but has the added feature of a second pair of brackets 554. The brackets 554 may have the features of bracket 554 of insert 550.

As shown in FIGS. 15A and 15B, it is possible to utilize insert 550' with the upper and lower brackets 554 along with frame 502 at one level, while utilizing insert 550 with a single pair of lower brackets 554 with frame 502 at an adjacent level. Thus, as illustrated, it is possible to stack multiple devices 500 by interchanging the components of the modular device 500 in order to create an ideal configuration that matches the anatomy of the cervical spine and allows multi-level stabilization without crowding.

FIGS. 16A-16D show another variation of device 500 in which the main frame 502' now includes two pairs of arms 504, 508. The upper arms 504 and lower arms 508 are similar in feature, and can contain screw holes 506 for receiving a bone screw such as, for example, the lateral mass screws 40 previously described. These arms 504, 508 may further be positioned adjacent to one another so as not to add unnecessary bulk to the overall frame 502'. The insert-receiving slot 510 of the frame 502' may still contain a rail 512 for mating with the groove 566 of the insert 550, 550', and as such, the mechanism of attaching the insert 550, 550' to the frame 502' remains the same as described above, and as illustrated in FIGS. 16C and 16D.

In the embodiments of FIGS. 12A, 12B, 13A, 13B, 14, 15A, 15B, and 16A-16D, these modular, two-part interlaminar, interspinous spinal stabilization devices enable an initially dynamic device to be converted into a fusion-enabling device by inserting the insert or sleeve into the dynamic device. The insert or sleeve thus acts to block the dynamic device from movement, thereby allowing subsequent fusion treatment of the spinal segment.

Figures 17A, 17B:
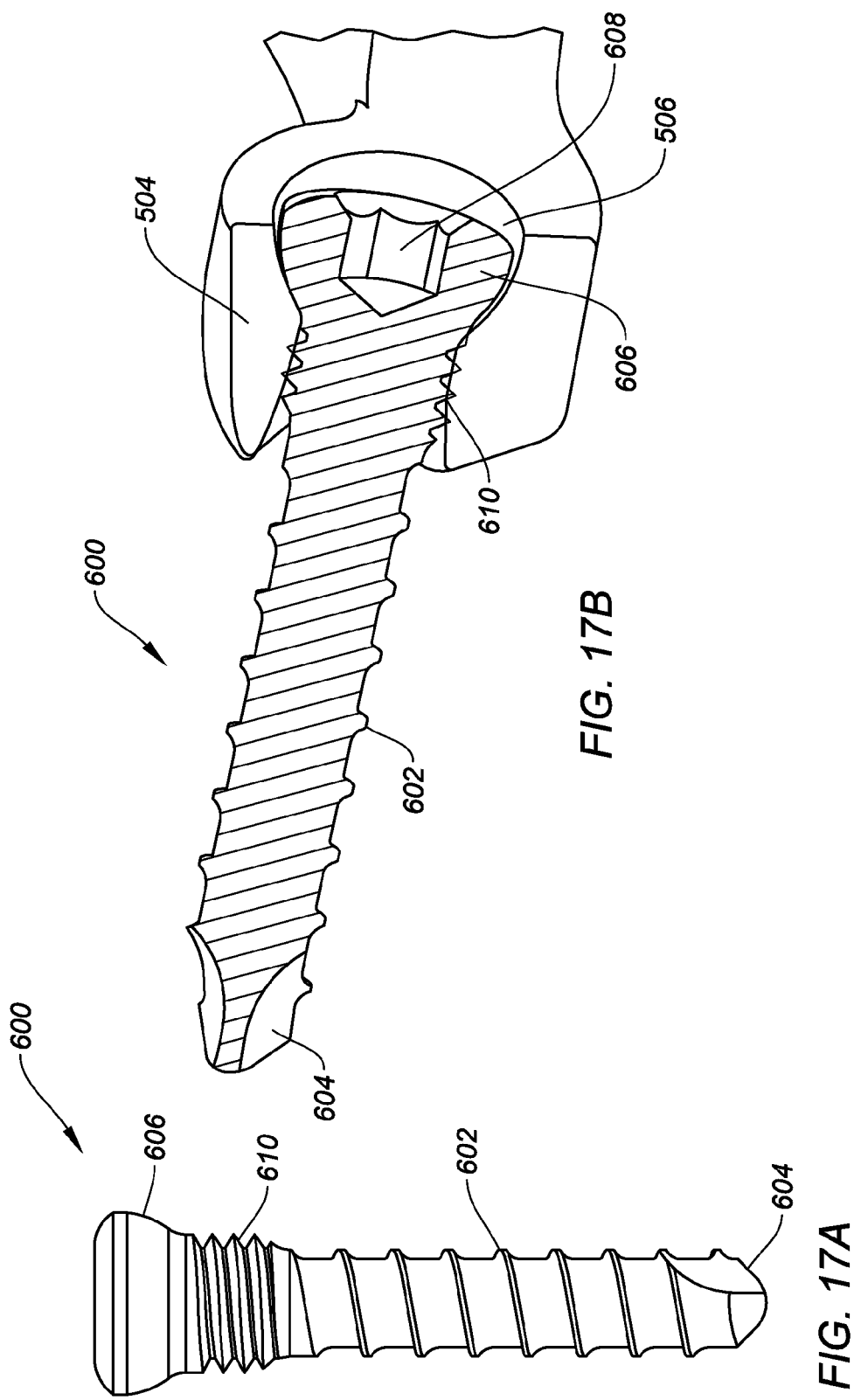
FIG. 17A shows a perspective view of an exemplary embodiment of a bone screw suitable for use with the interlaminar, interspinous spinal stabilization devices of the present disclosure.
FIG. 17B shows a partial cross-sectional view of the bone screw of FIG. 17A in use with a device of the present disclosure.

FIGS. 17A and 17B show an exemplary embodiment of a locking screw 600 of the present disclosure. The locking screw 600 may comprise a threaded shaft 602 that extends into a leading tip 604 at one end and a screw head 606 at the opposite end. The tip 604 may be self-tapping or self-leading. The screw head 606 may include a tool-engaging opening 608. In addition, the screw 600 may comprise self-cutting threads 610 adjacent the screw head 606, as shown. The self-cutting threads 610 enable the screw 600 to embed itself upon insertion into a PEEK screw hole 506, such as the one for main frame 502 of device 500, as illustrated in FIG. 17B. Such a screw 600 would be useful for any number of devices of the present disclosure.

FIGS. 18A and 18B show another exemplary embodiment of a locking screw of the present disclosure. The locking screw 700 may comprise a threaded shaft 702 that extends into a leading tip 704 at one end and a screw head 706 at the opposite end. The tip 704 may be self-tapping or self-leading. The screw head 706 may include a tool-engaging opening 708. In addition, the screw 700 may comprise spring tongues 710 adjacent the screw head 706, as shown. The spring tongues 710 enable the screw 700 to lodge itself upon insertion into a PEEK screw hole 506, such as the one for main frame 502 of device 500, as illustrated in FIG. 18B. Such a screw 700 would be useful for any number of devices of the present disclosure.

It is contemplated that the devices described and shown herein are useful for treatment of persistent neck pain and joint stress, such as that experienced following disc replacement surgery. Furthermore, the implant devices and their components may be linked together by fastening elements like screws (including overlapping screws), wire bands, ties, and the like, in order to provide an interconnected construct of multiple devices at multiple levels. Additionally, in some instances, small openings may be provided in the midline aspect of the devices provided herein to allow optional suturing of midline structures (e.g., muscle, fascia) during reconstruction of the soft tissues overlying the region.

It is understood that the devices of the present disclosure may be formed from a number of biocompatible materials, including the materials previously mentioned. For instance, the devices may be formed of a medical grade metal like titanium or a titanium alloy. The devices may also be formed from a variety of other materials, such as stainless steel, cobalt chrome, ceramics, and/or polymeric materials, such as ultra-high molecular-weight polyethylene (UHMWPE) and polyetheretherketone (PEEK), either alone or in combination with other suitable materials.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. An interlaminar, interspinous spinal stabilization device for stabilization of a cervical spine segment, comprising:

a unitary body configured for placement between adjacent cervical vertebrae, the body having an upper surface, a lower surface, and an insert portion therebetween, the lower surface having a pair of brackets extending at an obtuse angle therefrom relative to the body for receiving a spinous process of one of the adjacent cervical vertebrae; and a frame for attachment to the body, the frame having a pair of arms defining an elongate slot therebetween for receiving the insert portion of the body, and having at their free ends bone screw holes, the screw holes being angled and configured for receiving bone screws, wherein the upper and lower surfaces of the body are contoured to accommodate and support the cervical vertebrae.

2. The device of claim 1 wherein the bone screw holes extend along an upward angle relative to the arms.

3. The device of claim 1, wherein the pair of brackets comprise surface features for enhanced bone surface attachment.

4. The device of claim 3, wherein the surface features comprise teeth, barbs, spikes, ridges, bone-piercing protrusions, or surface roughenings.

5. The device of claim 1, wherein the pair of brackets include through-holes for receiving a rivet therethrough.

6. The device of claim 1, wherein the upper surface includes a second pair of brackets extending at an acute angle therefrom relative to the body.

7. The device of claim 1, wherein the pair of brackets are malleable.

8. The device of claim 1, wherein the upper surface further comprises a surface protrusion.

9. The device of claim 8, wherein the surface protrusion comprises a fin.

10. The device of claim 1, further including lateral mass bone screws for securing the device within the cervical spine segment.

11. The device of claim 1, wherein the body is configured for sliding engagement with the frame.

12. The device of claim 11, wherein the elongate slot of the frame includes a rail, and the insert portion of the body includes a groove for engagement with the rail.

13. The device of claim 1, wherein the body and frame are formed of the same material.

14. The device of claim 1, wherein the body and frame are formed of different materials.

* * * * *

UNITED STATES PATENT AND TRADEMARK OFFICE
CERTIFICATE OF CORRECTION

PATENT NO. : 10,278,745 B2
APPLICATION NO. : 14/940074
DATED : May 7, 2019
INVENTOR(S) : Graeme Woodworth, Stephen Eckhof and Sven Oliver Muckenfuß

Page 1 of 1

It is certified that error appears in the above-identified patent and that said Letters Patent is hereby corrected as shown below:

On the Title Page

In the Inventors (72)
Change "Stephen ECKHOF" to --Stephan ECKHOF--

Signed and Sealed this
Twenty-third Day of July, 2019

Andrei Iancu
*Director of the United States Patent and Trademark Office*